(12) United States Patent
Raman et al.

(10) Patent No.: US 12,076,168 B2
(45) Date of Patent: Sep. 3, 2024

(54) SYSTEM AND METHOD OF MEASURING VENOUS OXYGEN SATURATION USING INTELLIGENT PULSE AVERAGING WITH INTEGRATED EKG AND PPG SENSORS

(71) Applicant: HEMOCEPT INC., Seattle, WA (US)

(72) Inventors: Eric Raman, Seattle, WA (US); Kevin Peterson, Mountain View, CA (US); Iain Hueton, Salt Lake City, UT (US)

(73) Assignee: HEMOCEPT INC., Seattle, WA (US)

( * ) Notice: Subject to any disclaimer, the term of this patent is extended or adjusted under 35 U.S.C. 154(b) by 359 days.

(21) Appl. No.: 17/229,759

(22) Filed: Apr. 13, 2021

(65) Prior Publication Data

US 2021/0319892 A1 Oct. 14, 2021

Related U.S. Application Data

(63) Continuation of application No. 17/135,936, filed on Dec. 28, 2020.
(Continued)

(51) Int. Cl.
*A61B 5/00* (2006.01)
*A61B 5/0205* (2006.01)
(Continued)

(52) U.S. Cl.
CPC .......... *A61B 5/7285* (2013.01); *A61B 5/0006* (2013.01); *A61B 5/0036* (2018.08);
(Continued)

(58) Field of Classification Search
CPC . A61B 5/0006; A61B 5/0205; A61B 5/14552; A61B 5/282; A61B 5/349; A61B 5/02427; A61B 2562/146; G16H 40/63
See application file for complete search history.

(56) References Cited

U.S. PATENT DOCUMENTS 5,649,543 A 7/1997 Hosaka
5,795,300 A 8/1998 Bryars
(Continued)

FOREIGN PATENT DOCUMENTS

EP 1598004 12/2007
JP 2009-089883 A 4/2009
(Continued)

OTHER PUBLICATIONS

Vahdani-Manaf, Development of novel physiological analysis methods based on dual-wavelength photoplethysmographic signals time differences, J. Medical Imaging and Health Informatics, 6(2):372-9 (Apr. 2016).
(Continued)

*Primary Examiner* — Allen Porter
*Assistant Examiner* — Moussa Haddad
(74) *Attorney, Agent, or Firm* — MARSHALL, GERSTEIN & BORUN LLP

(57) ABSTRACT

A system using combined electrocardiography (EKG) and photoplethysmography (PPG) sensing, to determine venous oxygen saturation is described. The system uses averaging of similar pulses based on Prior (or n−1) R-to-R pulse wave duration, and current (or n) R-to-R pulse wave duration for evaluation of the metabolic reserve and/or stress of the patient.

15 Claims, 25 Drawing Sheets

Related U.S. Application Data

(60) Provisional application No. 63/067,147, filed on Aug. 18, 2020, provisional application No. 63/009,470, filed on Apr. 14, 2020.

(51) Int. Cl.

| | |
|---|---|
| *A61B 5/024* | (2006.01) |
| *A61B 5/145* | (2006.01) |
| *A61B 5/1455* | (2006.01) |
| *A61B 5/282* | (2021.01) |
| *A61B 5/349* | (2021.01) |
| *A61B 5/366* | (2021.01) |
| *G16H 40/63* | (2018.01) |
| *A61B 5/0245* | (2006.01) |

(52) U.S. Cl.
CPC ............ *A61B 5/004* (2013.01); *A61B 5/0205* (2013.01); *A61B 5/024* (2013.01); *A61B 5/14* (2013.01); *A61B 5/14552* (2013.01); *A61B 5/282* (2021.01); *A61B 5/349* (2021.01); *A61B 5/366* (2021.01); *A61B 5/4839* (2013.01); *A61B 5/6823* (2013.01); *A61B 5/6831* (2013.01); *A61B 5/6833* (2013.01); *G16H 40/63* (2018.01); *A61B 5/02427* (2013.01); *A61B 5/0245* (2013.01); *A61B 2560/0223* (2013.01); *A61B 2562/146* (2013.01)

(56) References Cited

U.S. PATENT DOCUMENTS

| | | | |
|---|---|---|---|
| 5,913,826 | A | 6/1999 | Blank |
| 6,527,724 | B1 | 3/2003 | Fenici |
| 6,527,728 | B2 | 3/2003 | Zhang |
| 6,805,673 | B2 | 10/2004 | Dekker |
| 7,402,138 | B2 | 7/2008 | Sugo |
| 7,502,643 | B2 | 3/2009 | Farringdon |
| 7,507,207 | B2 | 3/2009 | Sakai |
| 7,674,231 | B2 | 3/2010 | Mccombie |
| 7,738,936 | B1 | 6/2010 | Turcott |
| 7,920,919 | B1 | 4/2011 | Nabutovsky |
| 7,941,207 | B2 | 5/2011 | Korzinov |
| 8,447,374 | B2 | 5/2013 | Diab |
| 8,918,153 | B2 | 12/2014 | Cheng |
| 9,031,629 | B2 | 5/2015 | Park |
| 9,060,722 | B2 | 6/2015 | Teixeira |
| 9,254,095 | B2 | 2/2016 | Galloway |
| 9,538,949 | B2 | 1/2017 | Al-ali |
| 9,700,222 | B2 | 7/2017 | Quinlan |
| 10,010,276 | B2 | 7/2018 | Al-ali |
| 10,213,123 | B2 | 2/2019 | Hong |
| 10,278,647 | B2 | 5/2019 | Salehizadeh |
| 10,335,044 | B2 | 7/2019 | Banet |
| 10,398,381 | B1 | 9/2019 | Heneghan et al. |
| 10,469,241 | B2 | 11/2019 | Granqvist |
| 10,485,433 | B2 | 11/2019 | Baxi |
| 10,588,554 | B2 | 3/2020 | Poeze |
| 10,624,564 | B1 | 4/2020 | Poeze |
| 2005/0054905 | A1* | 3/2005 | Corl .................. A61B 5/14539 600/309 |
| 2006/0142665 | A1 | 6/2006 | Garay |
| 2007/0100219 | A1 | 3/2007 | Sweitzer |
| 2011/0270048 | A1 | 3/2011 | Addison |
| 2013/0066176 | A1 | 3/2013 | Addison et al. |
| 2013/0079606 | A1* | 3/2013 | McGonigle ........ A61B 5/14551 600/323 |
| 2014/0100432 | A1 | 4/2014 | Golda |
| 2014/0142445 | A1 | 5/2014 | Banet |
| 2014/0200415 | A1 | 7/2014 | Mccombie |
| 2014/0235964 | A1 | 8/2014 | Banet |
| 2014/0276143 | A1 | 9/2014 | Corl |
| 2014/0276145 | A1 | 9/2014 | Banet |
| 2015/0112154 | A1 | 4/2015 | He et al. |
| 2015/0182132 | A1 | 7/2015 | Harris |
| 2015/0196257 | A1* | 7/2015 | Yousefi .................. A61B 5/024 600/324 |
| 2015/0282722 | A1 | 10/2015 | Klepp |
| 2015/0313486 | A1 | 11/2015 | Mestha |
| 2016/0007895 | A1* | 1/2016 | Esenaliev ............ A61B 5/6814 600/309 |
| 2016/0066863 | A1 | 3/2016 | Thaveeprungsriporn et al. |
| 2016/0148531 | A1 | 5/2016 | Bleich et al. |
| 2016/0360986 | A1 | 12/2016 | Lange |
| 2018/0110432 | A1 | 4/2018 | Nam et al. |
| 2018/0279891 | A1 | 10/2018 | Miao et al. |
| 2018/0303355 | A1 | 10/2018 | Mccombie |
| 2018/0344177 | A1 | 12/2018 | Banet |
| 2018/0351120 | A1 | 12/2018 | Bao |
| 2018/0360325 | A1* | 12/2018 | Robinson ............. A61B 5/0205 |
| 2019/0059752 | A1* | 2/2019 | Botsva .................. A61B 5/332 |
| 2019/0076097 | A1 | 3/2019 | Edouard |
| 2019/0110363 | A1 | 4/2019 | Bao |
| 2019/0167130 | A1 | 6/2019 | Marchand |
| 2019/0183422 | A1 | 6/2019 | Moon |
| 2019/0216396 | A1 | 7/2019 | Mccombie |
| 2019/0229371 | A1 | 7/2019 | Song |
| 2019/0254524 | A1 | 8/2019 | Granqvist |
| 2019/0254540 | A1 | 8/2019 | Banet |
| 2020/0093389 | A1 | 3/2020 | Henry |
| 2020/0138316 | A1 | 5/2020 | Galloway |
| 2020/0163558 | A1 | 5/2020 | Baxi |

FOREIGN PATENT DOCUMENTS

| | | |
|---|---|---|
| WO | WO1998025516 | 6/1998 |
| WO | WO2006023924 | 3/2006 |
| WO | WO-2014/011368 A1 | 1/2014 |
| WO | WO2014042845 | 3/2014 |
| WO | WO-2017/217599 A1 | 12/2017 |
| WO | WO-2020/254882 A1 | 12/2020 |

OTHER PUBLICATIONS

Shafqat et al., Estimation of instantaneous venous blood saturation using the photoplethysmograph (PPG) waveform, Physiological Measurement, 36(10):1-14 (2015).

International Application No. PCT/US21/27161, International Search Report and Written Opinion, dated Aug. 20, 2021.

Reflectance pulse oximetry: Practical issues and limitations, Hooseok Lee, Hoon Ko, Jinseok Lee, ScienceDirect ICT Express 2 (2016) 195-198.

Pulse Transit Time and Blood Pressure During Cardiopulmonary Exercise Tests, T. Wibmer, K. Doering, C. Kropf-Sanchen, S. Rüdiger, I. Blanta, K. M. Stoiber, W. Rottbauer, C. Schumann Department of Internal Medicine II, University Hospital of Ulm, Ulm, Germany, Accepted Nov. 29, 2013, On-line Feb. 24, 2014.

Real-time aortic pulse wave velocitymeasurement during exercise stress testing Paul A. Roberts, Brett R. Cowan, Yingmin Liu, Aaron C. W. Lin, Poul M. F. Nielsen, Andrew J. Taberner, Ralph A. H. Stewart, Hoi Ieng Lam and Alistair A. Young,Roberts et al. Journal of Cardiovascular Magnetic Resonance (2015) 17:86; DOI 10.1186/s12968-015-0191-4.

Evaluation of pulse wave transit time analysis for non-invasive cardiac output quantification in pregnant patients Emmanuel Schneck, Pascal Drubel, Rainer Schürg, Melanie Markmann, Thomas Kohl, Scientific Reports | (2020) 10:1857 | https://doi.org/10.1038/s41598-020-58910-x Michael Henrich, Michael Sander & Christian Koch.

Continuous Estimation of Cardiac Output in Critical Care: A Noninvasive Method Based on Pulse Wave Transit Time Compared with Transpulmonary Thermodilution Ulrike Ehlers, Rolf Erlebach, Giovanna Brandi, Federica Stretti,Richard Valek, Stephanie Klinzing, and Reto Schuepbach, Critical Care Research and Practice vol. 2020, Article ID 8956372, 7 pages https://doi.org/10.1155/2020/8956372.

Extraction of respiratory signals from the electrocardiogram and photoplethysmogram: technical and physiological determinants; Peter H Charlton et al 2017 Physiol. Meas. 38 669.

(56) References Cited

OTHER PUBLICATIONS

Comparison between continuous non-invasive estimated cardiac output by pulse wave transit time and thermodilution method Ashish C. Sinha, Preet Mohinder Singh, Navneet Grewal, Mansoor Aman, Gerald Dubowitz Annals of Cardiac Anaesthesia vol. 17:Sep. 4-Dec. 2014.

Eko DUO ECG + Digital Stethoscope https://www.hopkinsmedicalproducts.com/electronic-stethoscopes.

Photoplethysmography for Quantitative Assessment of Sympathetic Nerve Activity (SNA) During Cold Stress https://www.frontiersin.org/articles/10.3389/fphys.2018.01863/full.

Ambulatory Pulse Wave Velocity Monitoring: A Step Forward DOI: 10.1161/HYPERTENSIONAHA.117.09121.) 2017 American Heart Association, Inc.

Development of a Low-Cost Wireless Phonocardiograph With a Bluetooth Headset under Resource-Limited Conditions Himel Mondal, Shaikat Mondal and Koushik Saha Med. Sci. 2018, 6, 117; doi:10.3390/medsci6040117.

Evaluation of Miniature Wireless Vital Signs Monitor in a Trauma Intensive Care Unit Jonathan P. Meizoso, MD; Casey J. Allen, MD; Juliet J. Ray, MD; Robert M. Van Haren, MD, MSPH; Laura F. Teisch, BS; Xiomara Ruiz Baez, MD; Alan S. Livingstone, MD; Nicholas Namias, MD, MBA; Carl I. Schulman, MD, Phd, MSPH; Kenneth G. Proctor, PhD Military Medicine, vol. 181, May Supplement 2016.

Towards Ubiquitous Blood Pressure Monitoring via Pulse Transit Time: Theory and Practice Ramakrishna Mukkamala IEEE Trans Biomed Eng. Author manuscript; available in PMC Aug. 1, 2015.

Cuff-Free Blood Pressure Estimation Using Pulse Transit Time and Heart Rate Ruiping Wang, Wenyan Jia, Zhi-Hong Mao, Robert J. Sclabassi, and Mingui Sun Int Conf Signal Process Proc. Oct. 2014 ; 2014: 115-118. doi:10.1109/ICOSP.2014.7014980.

Design and Prototyping of a Wristband-Type Wireless Photoplethysmographic Device for Heart Rate Vanability Signal Analysis M. Ghamari, Department of Electrical and Computer Engineering, University of Texas at El Paso, El Paso, Texas, USA Conf Proc IEEE Eng Med Biol Soc. Author manuscript; available in PMC Sep. 26, 2017.

Pulse Oximetry, Book Chapter.

Novel Methods for Pulse Wave Velocity Measurement Tania Pereira, Carlos Correia, Joao Cardoso J. Med. Biol. Eng. (2015) 35:555-565 DOI 10.1007/s40846-015-0086-8.

Ability of esCCO to track changes in cardiac output M. Biais, R. Berthezène, L. Petit, V. Cottenceau and F. Sztark British Journal of Anaesthesia, 2015, 403-10 doi: 10.1093/bja/aev219.

Pulse oximetry: Understanding its basic principles facilitates appreciation of its limitations Edward D. Chan, Michael M. Chan, Mallory M. Chan Respiratory Medicine (2013) 107, 789e799.

W-H, Tsai T-H, et al. (2016) Modeling the Pulse Signal by Wave-Shape Function and Analyzing by Synchrosqueezing Transform. Plos ONE 11(6): e0157135. doi:10.1371/journal.pone.0157135.

PPG and ECG feature comparison for healthy people and hypertensive patients Jan. 2012 DOI:10.1109/BHI.2012.6211701.

Precision wearable accelerometer contact microphones for longitudinal monitoring of mechano-acoustic cardiopulmonary signals Pranav Gupta, Mohammad J. Moghimi, Yaesuk Jeong, Divya Gupta, Omer T. Inan and Farrokh Ayazi npj Digital Medicine vol. 3, Article No. 19 (2020).

Pulmonary Artery Catheterization, 2020 up to Date, Inc.

Pulse oximetry, 2020 up to Date, Inc.

Oxygen Saturation Measurements from Green and Orange Illuminations of Multi-Wavelength Optoelectronic Patch Sensors Samah Alharbi, Sijung Hu, David Mulvaney, Laura Barrett, Liangwen Yan, Panagiotis Blanos, Yasmin Elsahar and Samuel Adema Sensors 2019, 19, 118; doi:10.3390/s19010118.

Standard Terminologies for Photoplethysmogram Signals, DOI: 10.2174/157340312803217184.

Wearable Solutions for Improving Heart Health and Wellness PPG vs. ECG-based Biosensors: The Pros and Cons NeuroSky.

Cox et al., Investigation of photoplethysmogram morphology for the detection of hypovolemic states, Engineering in Medicine and Biology Society, 30th Annual International Conference of the IEEE, 5486-5489 (Aug. 2008).

European Patent Application No. 21788309.9, Extended European Search Report, dated Jan. 22, 2024.

European Patent Application No. 21788382.6, Extended European Search Report, dated Jan. 25, 2024.

Marks et al., Stockwell Transform Detector for Photoplethysmorgraphy Signal Segmentation, 52nd Asilomar Conference on Signals, Systems and Computers, IEEE, 1239-1243 (Oct. 2018).

* cited by examiner 401    402

Select, based on:

prior RtoR = $RtoR_{n-1}$
or
current RtoR = $RtoR_n$

⬇

Multiple Pulse Data Sets. PPG signals for each wavelength are averaged and a Composite Pulse Data Set is constructed with the new PPG signal data for each wavelength

⬇

$PPGSignal_{Red, IR, Green}[t \geq t0_n]$ :

$SPOS_{Red, IR, Green}[t \geq t0_n]$ :

$PWTT_{Red, IR, Green} = t_{SPOSmin} - t0_n$ :

801   802 red composite pulse, count = 8, prior_r2r = 0.898

$PPGSignal_{Red}$ ir composite pulse, count = 8, prior_r2r = 0.898

$PPGSignal_{IR}$ green composite pulse, count = 8, prior_r2r = 0.898

$PPGSignal_{Green}$

Composite Pulse Data Set

FIG. 8

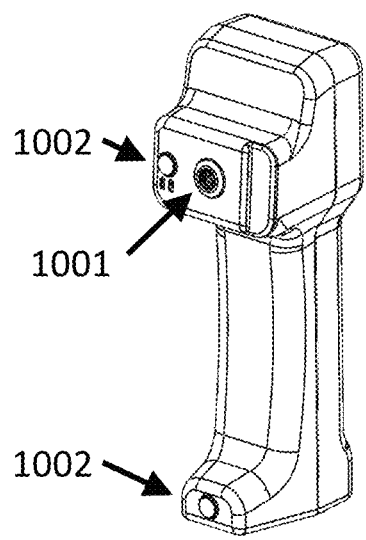
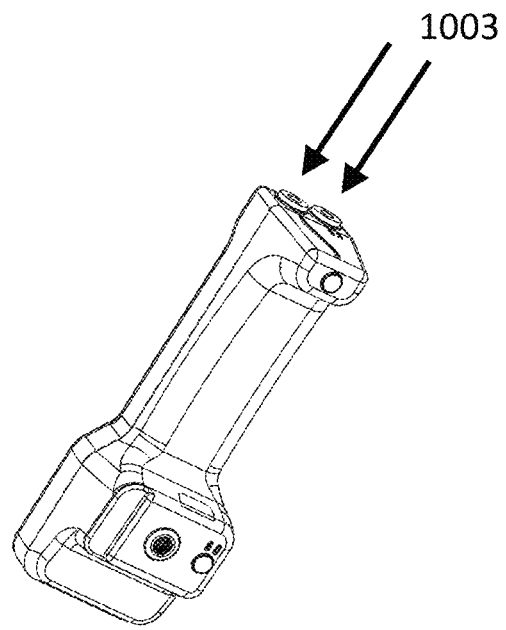
FIG. 10A FIG. 10B
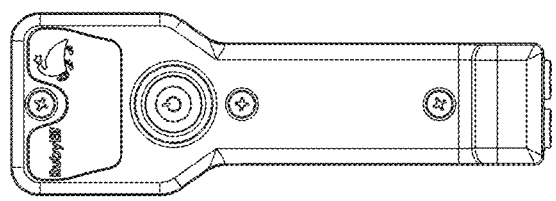
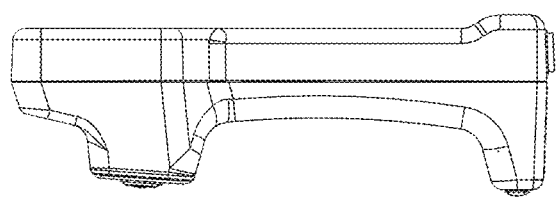
FIG. 10C FIG. 10D

|  | n-1 R-to-R | | |
|---|---|---|---|
|  | short | intermediate | long |
| short n | [286, | 26, | 3] |
| Intermediate n | [ 60, | 215, | 59] |
| long n | [ 3, | 103, | 225] |

```python
def prune_comp(comp, pulse_bin):
    PWTT_THRESHOLD = 0.15
    while True:
        comp.calc_pwtt()

# compare PWTT of composite to that of each pulse
        comp_pwtt_red = comp.pwtt['red']
        comp_pwtt_ir = comp.pwtt['ir']
        comp_pwtt_green = comp.pwtt['green']

red_pwtt_threshold = comp_pwtt_red * PWTT_THRESHOLD
        ir_pwtt_threshold = comp_pwtt_ir * PWTT_THRESHOLD
        green_pwtt_threshold = comp_pwtt_green * PWTT_THRESHOLD pruned_pulse = None
        for pulse in pulse_bin:
            red_exceeds_threshold = np.abs(pulse.pwtt['red'] - comp_pwtt_red) > red_pwtt_threshold
            ir_exceeds_threshold = np.abs(pulse.pwtt['ir'] - comp_pwtt_ir) > ir_pwtt_threshold
            green_exceeds_threshold = np.abs(pulse.pwtt['green'] - comp_pwtt_green) > green_pwtt_threshold
            majority_exceeds_threshold = (red_exceeds_threshold and ir_exceeds_threshold or
                                          ir_exceeds_threshold and green_exceeds_threshold or
                                          red_exceeds_threshold and green_exceeds_threshold)
            if majority_exceeds_threshold:
                # prune this pulse and try again
                pruned_pulse = p
                break if not pruned_pulse:
            break
        else:
            pulse_bin.remove(pruned_pulse)
            comp.sub(pruned_pulse)

# nothing left, done for now
        if comp.count == 0:
            break
```

FIG. 19

SYSTEM AND METHOD OF MEASURING VENOUS OXYGEN SATURATION USING INTELLIGENT PULSE AVERAGING WITH INTEGRATED EKG AND PPG SENSORS

RELATED APPLICATIONS

The present application claims priority to U.S. Provisional Patent Application Ser. No. 63/009,470, entitled PULSE WAVE TRANSIT TIME (PWTT) MEASUREMENT SYSTEM USING INTEGRATED EKG AND PPG SENSORS, filed Apr. 14, 2020, and to U.S. Provisional Application Ser. No. 63/067,147, entitled, SYSTEM FOR IMPROVED MEASUREMENT OF OXYGEN SATURATION, NON-INVASIVE DETECTION OF VENOUS AND ARTERIAL PULSE WAVEFORMS, AS WELL AS DETECTION OF CARBOXYHEMOGLOBIN, HYPERTROPHIC CARDIOMYOPATHY AND OTHER CARDIAC CONDITIONS, filed Aug. 18, 2020, and to U.S. patent application Ser. No. 17/135,936, entitled SYSTEMS FOR SYNCHRONIZING DIFFERENT DEVICES TO A CARDIAC CYCLE AND FOR GENERATING PULSE WAVEFORMS FROM SYNCHRONIZED ECG AND PPG SYSTEMS, filed Dec. 28, 2020, the entire disclosures of which are incorporated herein by reference in their entireties for all purposes.

TECHNICAL FIELD OF THE INVENTION

The present system relates to cardiac sensing systems using combined electrocardiographic (EKG) and photoplethysmographic (PPG) sensing systems.

Brief Description of the Clinical Problem

Venous hemoglobin oxygenation in health is often greater than 80%. While this may seem surprising, this high level of oxygenation represents a metabolic reserve that the body can dip into even though a deep breath has not been taken in the last few seconds. In states of stress that reserve will be whittled away; as such venous saturation is clinically useful as it provides a measure of the body's oxygen reserve. Currently this can only be obtained via an invasive venous blood gas measurement. Venous oxygen saturation and serum lactate are both used to measure a patient's degree of metabolic reserve and stress, as venous saturation is depressed in times of metabolic stress. Serum lactate will rise when tissues are not receiving sufficient oxygen to meet the metabolic needs, and the tissues turn to anaerobic use of glucose. Currently, the most common measure for evaluation of metabolic stress is a serum lactate, though recent studies such as *Serum Lactate Poorly Predicts Central Venous Oxygen Saturation In Critically Ill Patients: A Retrospective Cohort Study* by Bisara et. al., PMID: 21516712, DOI: 10.1186/s40560-019-0401-5, suggest venous oxygen saturation may be a better early measure of stress before onset of critical decompensation. Serum measurement of lactate, or a venous blood gas, requires aseptic blood drawing capacity and a qualified laboratory nearby capable of expeditiously running a venous sample that has been put on ice after blood draw. The capability of non-invasively measuring venous oxygenation saturation therefore has tremendous implications for assessing metabolic stress in both resource-rich and resource-limited situations.

Summary of the Invention and Cardiac Physiology Germane to the Invention

In preferred aspects, the present system determines venous oxygen saturation in a system that comprises: (a) a device positionable against a person's skin; (b) at least one PPG sensor mounted on the device for measuring the person's PPG signal at multiple wavelengths of light; (c) a plurality of electrodes for measuring the person's EKG signal; (d) a computer logic system for receiving and analyzing the PPG signal and the EKG signal, wherein the computer logic system further comprises: (i) a system for identifying cardiac cycles in the EKG signal; (ii) a system for segmenting the PPG signal into a series of PPG signal segments based upon features in the identified cardiac cycles, (iii) a system for sorting the PPG signal segments into a plurality of bins, each bin based upon durations of prior R-to-R cardiac cycles and current R-to-R cardiac cycles, (iv) a system for generating a composite signal for each of the plurality of bins, and (v) a system for measuring a person's venous oxygen saturation by: (a) calculating arterial oxygen saturation by comparing composite signals measured at different wavelengths of light, (b) sub-sampling composite signals at two consecutive signal maxima measured at different wavelengths of light, and (c) comparing the sub-sampled composite signals measured at different wavelengths of light to the calculated arterial oxygen saturation to determine venous oxygen saturation. Preferably, the arterial oxygen saturation is calculated by comparing composite signals measured at different wavelengths of light which comprises comparing composite Signal Prime Over Signal (SPOS) signals, each composite SPOS signal being the derivative of a composite signal normalized by the composite signal itself.

In preferred aspects, the present system for measuring a person's venous oxygen saturation selects preferred bins from which the composite signals are used when calculating the person's venous oxygen saturation, and the preferred bins correspond to the bins having the largest number of PPG signal segments therein and/or the largest difference between current and prior R-to-R values. A composite signal may be generated for each bin by summing or averaging the PPG signal segments in the bin. In addition, the composite signal may be used to generate a composite Signal Prime Over Signal (SPOS) which is the derivative of the composite signal normalized by the composite signal itself. In such aspects, a system for calculating arterial oxygen saturation by comparing composite SPOS signals measured at different wavelengths of light may be included.

In preferred aspects, the system for generating a composite signal for each of the plurality of bins comprises a system for removing aberrant PPG signal segments from the calculation of the composite signal, for example, by iteratively re-calculating the composite signal, by: comparing a SPOS of each of the PPG signal segments used to calculate a composite signal against the SPOS of the calculated composite signal, removing outlier PPG signal segments, re-calculating the composite signal with the outlier PPG signal segments removed, and repeating the iteration until there are no more outlier PPG signal segments.

In various preferred physical embodiments illustrated herein, the present system is a hand-held device with the at least one PPG sensor mounted thereon and a plurality of electrode wires extending therefrom or mounted thereon. Alternatively, the present system may be positioned within a strap or band disposed around the person's chest or limb with at least one PPG sensor and the plurality of electrodes are disposed within the strap or band. Alternatively, the present system may be disposed in a patch with the at least one PPG sensor and at least one of the plurality of electrodes positioned therein. Systems are also provided for data transmission.

The present system provides information regarding the metabolic reserve/stress of a given patient, inexpensively and non-invasively. Such knowledge can provide clinicians with critical point-of-care information about the clinical trajectory of a patient's recovery or decline quickly and safely, without having to wait on laboratory results. At heart is the analysis of FIG. 1 showing the system top-level flow diagram for estimating venous saturation, wherein the hemoglobin saturation of arterial blood is obtained from the main-pulse region of a composite PPG signal shape (101), i.e. the region of greatest slope change, and a separate estimation of venous blood hemoglobin oxygenation is obtained using only end-pulse signal maxima/arterial pulse minima (102). The two results are then compared to determine how much oxygen reserve is apparent.

The key to this analysis is understanding that the dynamics of the "tissue sandwich", through which the PPG signal is filtered, changes slightly at the end of the pulse. This seen in FIG. 2. The curve 201 is an experimentally obtained arterial waveform, derived from a composite IR PPG signal. As one can see, the waveform is incredibly clean, the result of intelligent similar pulse averaging over a number of minutes. The salient point is that, were the arterial pulse descent from the peak (or "roll-off") a simple exponential, or even a steady decline, the curve would not result in the "hump" seen prior to the pulse minimum just prior to the onset of the next pulse (202).

Rather than passive draining, in this time frame there is active filling of arterioles, in essence priming an "hour glass" structure consisting of the arterioles, capillaries (through which blood cells pass one-by-one), and venules. This priming effect causes a change in the composition of the blood measured by PPG oximetry. Capitalizing on this observation, that the blood composition is changing just prior to the end of the pulse, signal maxima (corresponding to arterial pulse minima) are gathered together and analyzed independently from the PPG signal obtained through the pulse. A pictorial depiction of this approach is provided in FIG. 3, showing LED sampling in FIG. 3A, standard PPG arterial hemoglobin oximetry, and FIG. 3B end-pulse/signal maxima sampling. Line 302 shows the arterial pulse sampled via standard oximetry, through which LED signal (301) sampling occurs. Line 303 is the resultant PPG signal. Point 304 shows a signal maxima/pulse minima. FIG. 3B shows the different sampling done in end-pulse/signal maxima oximetry. Line 306 shows the arterial pulse, through which LED signal (305) sampling occurs, though only at end-pulse, signal maxima. Line 307 is the resultant PPG signal with such sampling.

Further depiction of the structure being measured at arterial end-pulse can be seen in FIG. 4. In FIG. 4A the arteriole/capillary/venule structure is shown as an hourglass. Through the main portion of the arterial pulse, an hourglass representing the arteriole/capillary/venule structure measured in reflective oximetry is dominated by the maximally oxygenated, pre-capillary arteriole blood (401). However, at end-pulse there is piling up of the venule, post-capillary blood, depicted in 402. FIG. 4B gives another representation of the structure, with the structure measured in reflective oximetry is shown as a shaded area (403). Also seen is a graph with a curve of the velocity of blood movement (404). This shows the blood cells slowing to their lowest velocity as they pass through the capillaries, with an asymmetry in velocity prior and post capillaries, explaining the change in arteriole to venule blood at end-pulse.

The approach is further explained in FIGS. 5A and 5B, showing changes between the sampling points (the R-to-R duration) as linear, and how the PPG signal may change. Area 501 shows the end-pulse arterial (pre-capillary) blood, and area 502 the end-pulse venous (post-capillary) blood; area 503 is the fixed elements of the structure (largely connective tissue). In FIG. 5A LED sampling through the structure at end-pulse/signal maxima (504) before and after long pulses yields PPG signals 505 and 506, separated by time 507 (R-to-R duration). In FIG. 5B LED sampling through the structure at end-pulse/signal maxima (504) before and after short pulses yields PPG signals 508 and 509, separated by time 510 (R-to-R duration).

The present system uses combined electrocardiography (EKG) and photoplethysmography (PPG) signals (PPG is also commonly referred to as oximetry and the two terms will be used interchangeably throughout this specification). The former senses voltage produced by heart muscle contraction, and the latter measures light absorbed by tissues. Changes in PPG signal reflect changes in blood volume and measurement at different wavelengths allows determination of oxygen saturation.

The present system allows different insight than is currently available using hand-held, portable PPG systems/devices. The combination of EKG and PPG signals in this system utilize Pulse Wave Transit Time (or PWTT), and PPG Signal Prime Over Signal (SPOS) curves. PWTT is the period of time taken between a heartbeat as measured by the onset of the QRS complex and the time at which the blood from the aorta reaches an extremity or other body part, as determined by the negative spike generated in the SPOS curve, also described as the derivative of the LED signal divided by the signal. Use of the signal derivative to determine the change in a LED signal heralding the arrival of an arterial pulse has been described in U.S. Pat. No. 10,213,123, assigned to MocaCare Corporation of Palo Alto, California, however use of the signal prime over signal (SPOS) allows for greater insight, as it normalizes each wavelength signal and thus allows for comparisons between different wavelength SPOS curves.

Improved arterial oxygen saturation estimation is then generated by this system from an SPOS curve using a composite sum/average of similar pulses, with the added ability to generate oxygen saturation for selected segments of the cardiac cycle, specifically end-pulse oximetry. Prior (n−1) EKG R-to-R duration using R-wave peaks are calculated, as are Current (n) R-to-R duration, PWTT, and SPOS. These are all used by the present system to determine similarity of oximetry pulses, with similar pulses summed/averaged to form composite pulses, then comparing differing composite pulses to gain cardiovascular insight.

Reduced PWTT corresponds to greater pulse wave velocity, though the greater velocity does not indicate better pump function. This is because the aortic bulb acts as a "mechanical capacitor", allowing metered delivery of arterial pulse volume. However, having obtained the PWTT for any given monitoring point on the body, this metric remains relatively stable and changes only gradually barring a sudden change in cardiovascular state (e.g. sudden change in heart rhythm such as onset of atrial fibrillation with rapid ventricular response). PWTT therefore provides a means by which to ensure accurate further data collection and analysis. This allows more reliable extraction of additional information from the combination of signals, and removal/minimization of introduced noise.

Measurement of absorption of light (per Beer-Lambert law) has the form Measurement$(t) = Ke^{[-Cf(t)]}$, and the signal prime over signal (SPOS) of the measurement will be:

$$SPOS(t) = -C\left(\frac{df(t)}{dt}\right).$$

The LED signals in plethysmography have the form:

$$\text{Signal} = K * e^{[-Arterial(t)*\Sigma(\alpha*Hb)_{arterial}]} * e^{[-Venous(t)*\Sigma(\alpha*Hb)_{venous}]} \quad (1)$$

$\Sigma(\alpha*Hb)_{arterial}$ and $\Sigma(\alpha*Hb)_{venous}$ describe the composition of the blood and generally change slowly. Therefore, these two terms are constants across time for the duration of our sampling. (These terms will be explained in greater detail herein).

Further, in healthy individuals, the venous flow is considered a constant. Current oximetry measures assume this, and so will we for this initial exploration. Given this assumption, the equation reduces to:

$$\text{Signal} = K_1 * e^{[-Arterial(t)*\Sigma(\alpha*Hb)_{arterial}]} \quad (2)$$

Using properties of the exponential function, and of its derivative, we derive the SPOS for the PPG Signal at several wavelengths (e.g., IR and Red).

$$SPOS(t) = -\left(\frac{dArterial(t)}{dt}\right) * \sum(\alpha*Hb)_{arterial} \quad (3)$$

Using the fact that the conceptual function Arterial(t) is the same for both Red and IR PPG signals, we show that the SPOS of the signal from the IR LED ($SPOS_{IR}$) is directly proportional to the SPOS of the signal from the Red LED ($SPOS_{Red}$):

$$SPOS_{Red} = R * SPOS_{IR} \text{ or } SPOS_{Red}/SPOS_{IR} = R \quad (4)$$

Returning to the expression $$\sum\left(\alpha_{\mu Hb_x} * Hb_x\right)$$

This describes how different wavelengths of light are absorbed by the blood depending on the relative quantity of the types of hemoglobin present within.

Where:

$\alpha_{\mu Hb_x}$ = absorption coefficient for type of hemoglobin (deoxyhemoglobin, oxyhemoglobin, carboxyhemoglobin, methemoglobin), x, for the wavelength, $\mu$ $Hb_x$=fractional composition of blood of various types of hemoglobin. The Sum of fractional components of different types of hemoglobin=1.0

In the conditions of low levels of carboxyhemoglobin and methemoglobin (e.g. excepting situations such as carbon monoxide or cyanide poisoning), and using accepted standard absorption coefficients for $\alpha_{IR_{Hb}}$, $\alpha_{Red_{Hb}}$, $Hb=1-Hb_{O_2}$.

We end up with the equation:

$$\left(\alpha_{Red_{HbO_2}} * Hb_{O_2}\right) + \left(\alpha_{Red_{Hb}} * (1 - Hb_{O_2})\right) = \quad (5)$$

$$R * \left[\left(\alpha_{IR_{HbO_2}} * Hb_{O_2}\right) + \left(\alpha_{IR_{Hb}} * (1 - Hb_{O_2})\right)\right]$$

The only unknown is $Hb_{O_2}$. Solving for $Hb_{O_2}$ gives us the fraction of the blood that is oxygenated (Arterial oxygenated hemoglobin Fraction, or Arterial Frac O2):

$$\text{Arterial Frac } O_2 = \frac{(-\alpha_{IRHb} * R + \alpha_{RedHb})}{R * (\alpha_{IRHbO_2} - \alpha_{IRHb}) + (\alpha_{RedHb} - \alpha_{RedHbO_2})} \quad (6)$$

This direct proportionality between SPOS for any wavelength and the summation of optical absorption coefficients times the fraction of hemoglobin is used extensively by the present system.

Any recording of EKG, or oximetry signals, or their interaction, will have physiologic variability, as well as noise. Management of EKG noise have established protocols that have been built up over 100 years. Conditioning of oximetry signals do not have as long a history. Physiologic oximetry variability can occur from changes in venous flow (due to volitional movement, or passive movement from repositioning, or inflation/deflation of a blood pressure cuff/sphygmomanometer, etc.), respiration causing changes in intra-thoracic pressure with resultant change in blood volume return to the heart, or beat-to-beat duration variability. Noise, or non-physiologic variability, can also occur from a range of possibilities, from variation in the surface pressure and angle of application of the detector, to ambient light infection of signal collection, to DC drift of the detection circuit. Whatever the specific source of variation, without an intelligent approach to the signals, one cannot tell physiologic variability apart from non-physiologic variability (introduced noise).

Traditional means for dealing with noise introduced into oximetry signals is to filter. For example, a commonly used algorithm for detecting signal to noise ratio utilizes power within the frequencies below 20 Hz compared with power above this frequency (as described in MaximIntegrated AppNote AN6410.pdf provided by Maxim Integrated Corporation of San Jose, California). This frequency filtering highlights the underlying primary rhythm (heart rate) and smooths the appearance of the displayed waveform. However, pulses are not all the same, and treating them as if they are deletes valuable information that can be mined for deeper insight.

An alternative means by which to minimize variability is to average the oximetry over many pulses, as described in U.S. Pat. No. 10,485,433, assigned to Intel Corporation. This allows for minimization of introduced noise, but eliminates any information that could be gleaned from physiologic variability. This approach produces a single, homogenized, and representative pulse at the end of the process. However, pulses are not all the same, and treating them as if they are effectively obliterates some of the available information.

With the observation of FIG. 2, a re-evaluation of the assumption of a flat venous blood profile (as in equation (1)) can be done. The combination of more or less arteriole filling/emptying and more or less right ventricular filling with differing R-to-R will be seen in varying PPG signal maxima, with both venule volume and arteriole volume changing at signal maxima (FIG. 5). The ratio of arteriole and venule composition in this delta volume is not yet entirely clear. However, the approach shows that an enlarging difference between end-pulse oximetry and arterial hemoglobin oxygen saturation calculated from the rising pulse (main-pulse oximetry) reflects falling venous hemoglobin oxygen saturation.

BRIEF DESCRIPTION OF THE DRAWINGS

FIG. 8 also shows the nomenclature and data structures used in the description of the present system.

FIGS. 10A to 10D show various views of a hand-held embodiment of the present system, having PPG and EKG sensors mounted thereon or attached thereto.

FIG. 19 is a is an exemplary algorithm for preparing Pulse Data Sets in accordance with the present system.

DETAILED DESCRIPTION OF THE INVENTION

The central element of the system is the identification and manipulation of PPG signals on the basis of Prior R-to-R and Current R-to-R duration. The system them generates composite pulses from similar pulses.

In accordance with preferred aspects disclosed in U.S. Provisional patent application 62/955,196, entitled A System For Synchronizing Different Devices To A Cardiac Cycle, filed Dec. 30, 2019 and in U.S. patent application Ser. No. 17/135,936, entitled SYSTEMS FOR SYNCHRONIZING DIFFERENT DEVICES TO A CARDIAC CYCLE AND FOR GENERATING PULSE WAVEFORMS FROM SYNCHRONIZED ECG AND PPG SYSTEMS, filed Dec. 28, 2020, incorporated herein by reference in their entireties, the present system uses a specific trigger to set time=0 for each beat (e.g. EKG R-wave peak) and then stores each pulse from this start point until completing a full cycle of sensor data, such as with LED oximetry signals from maximum to minimum and back to maximum—which will be a waveform longer than a single pulse length. The next pulse waveform will have a t=0 at the next EKG R-wave peak, thus recording of the next beat will start before the recording of the last pulse waveform has completed. In absolute terms, the time corresponding to t=0 for the nth pulse will be referred to as time t0n throughout the rest of the specification.

Figure 6:
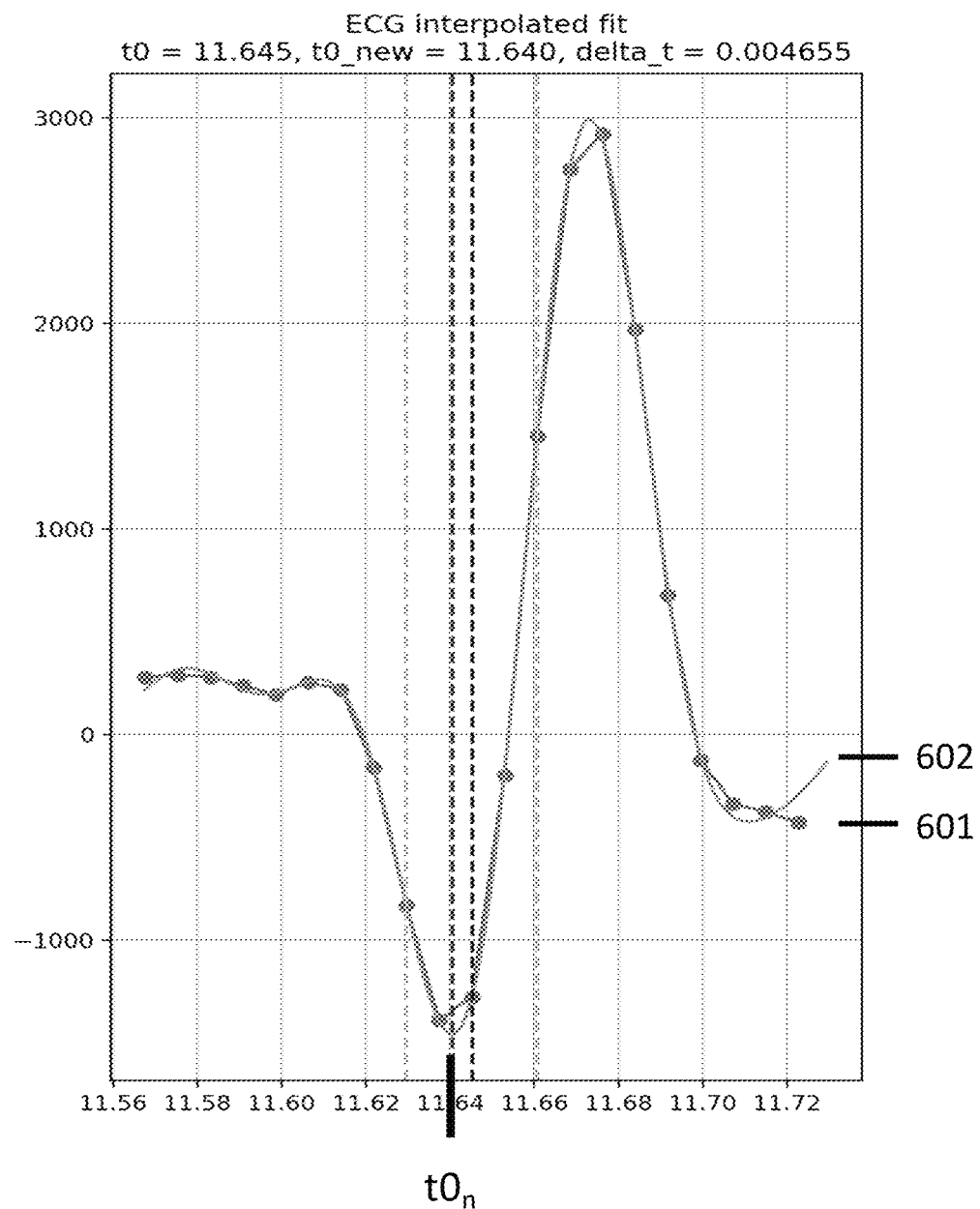
FIG. 6 shows the process of R-wave peak refinement used to generate t0n.

FIG. 6 shows the process of R-wave peak refinement used to generate t0n. The example shows how the algorithm has determined the polarity of this collection to be negative (wires reversed), and thus the R-wave to be negative. The t0n of the R-wave peak is found using polynomial fitting (602) to EKG datapoints (601) and interpolation, then used to define a Pulse Data Set.

Figure 7:
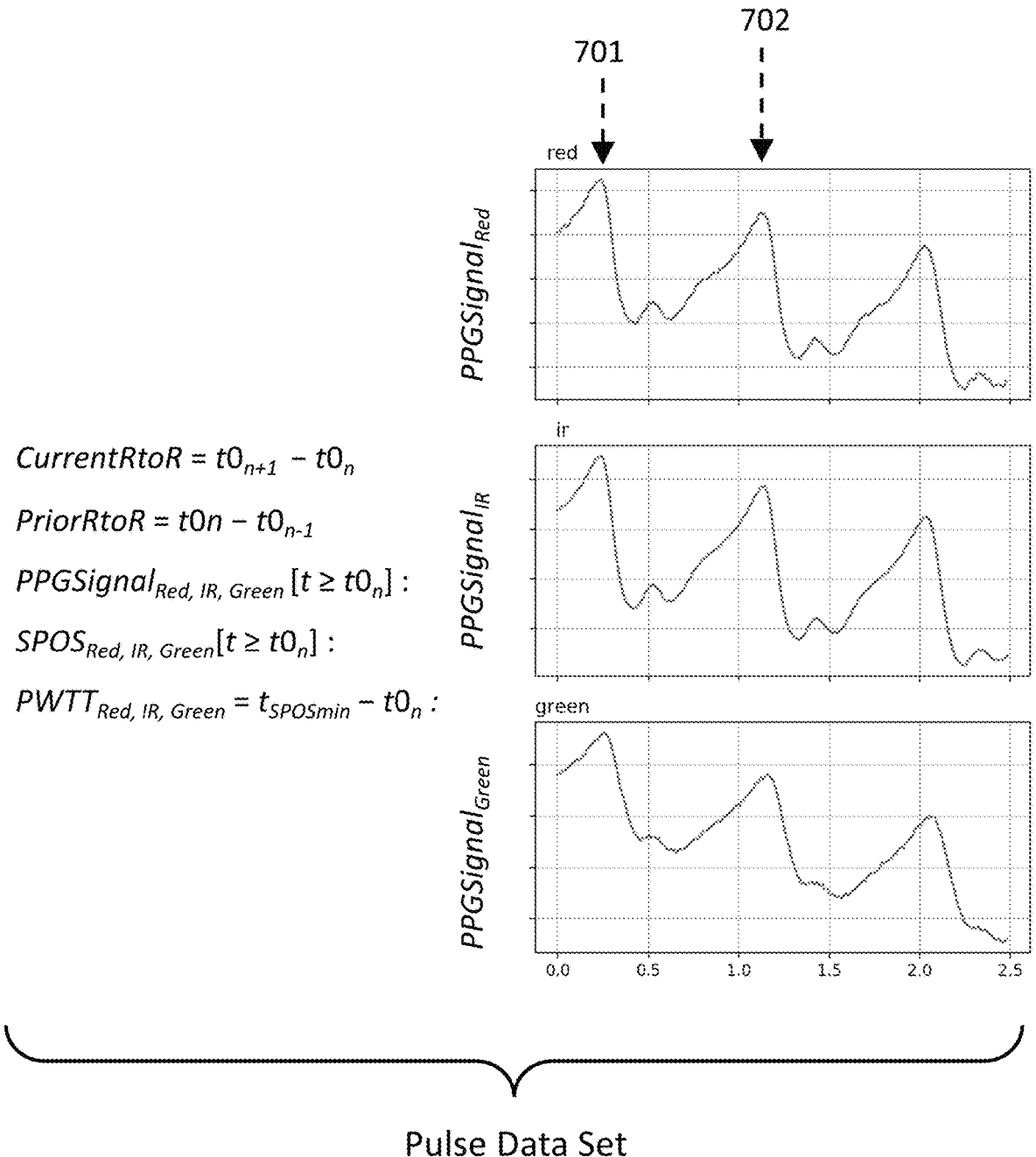
FIG. 7 shows the nomenclature and data structures used in the description of the present system.

FIG. 7 and FIG. 8 show the nomenclature and data structures used in the description (Unless otherwise specified, PWTT=PWTTIR and PPG signal=PPG signalIR). The t0n time point is then used to define a Pulse Data Set with the PPG signals of multiple wavelengths (here red, infrared, and green). Stored with the PPG signal are the values for the prior R-to-R, and current R-to-R durations, the derived signals for Signal Prime over Signal (SPOS) for each wavelength, and the Pulse Wave Transit Time (PWTT) for each wavelength. Note the first PPG signal maxima (701) and the second PPG signal maxima (702). FIG. 8 shows the structure of the Composite Pulse Data Set, constructed from a group of Pulse Data Sets on the basis of a defined criteria (e.g. similar prior R-to-R, or current R-to-R duration). Note how the PPG waveforms are of duration longer than a single cardiac cycle, and are long enough to assure capture of both the first (801) and second PPG signal maxima (802).

Figure 9:
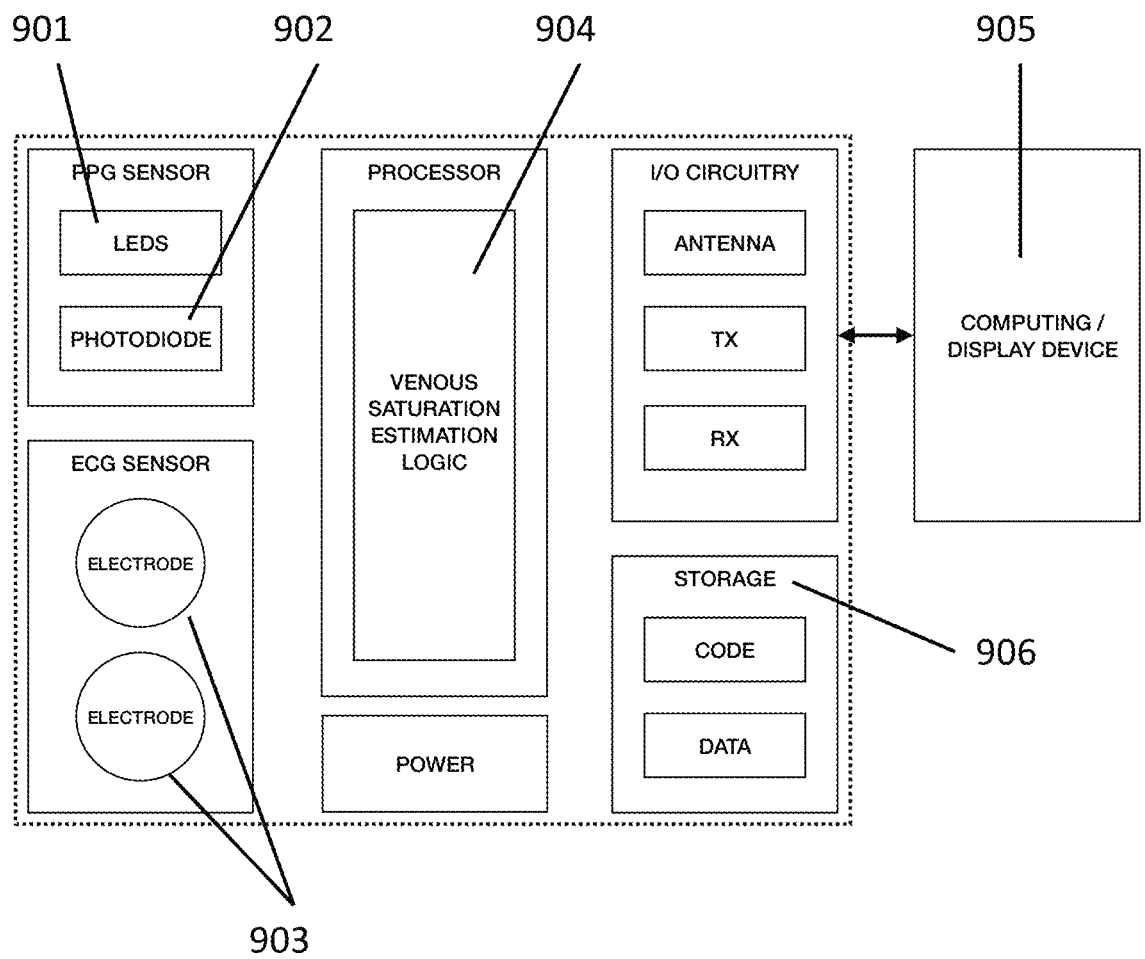
FIG. 9 is an exemplary illustration of various physical components of the present system.
Figure 11:
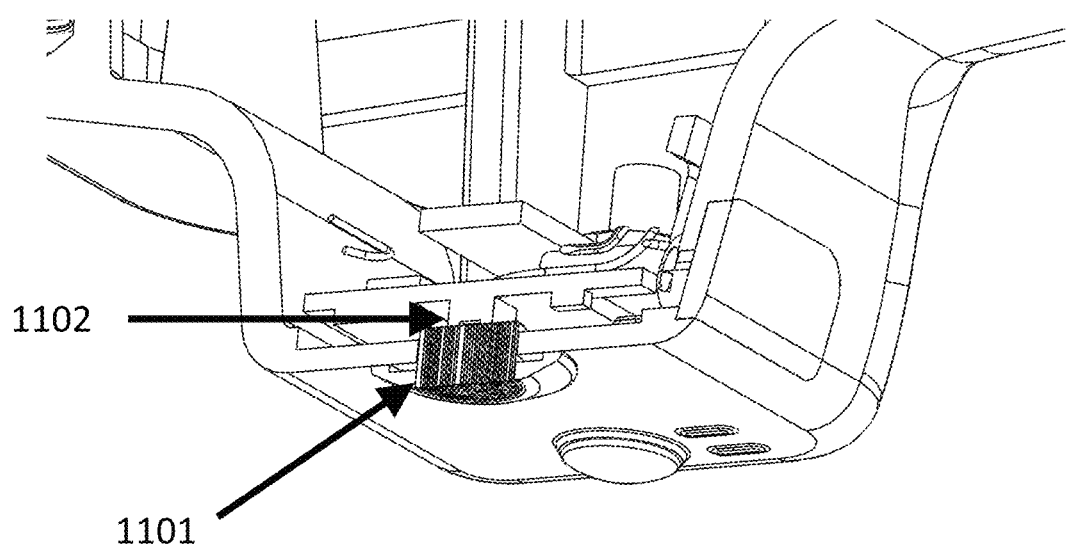
FIG. 11 is a is a cut-away view of a portion of the device of FIGS. 10A to 10D, showing an optical waveguide adjacent to a PPG sensor.

FIGS. 9-11 show a preferred device implementation of the system. The device block diagram shows the elements of the device/system, with multiple wavelength LEDs (901) and a photodiode detector (902), and EKG input from electrodes (903) applied to the left and right chest (or left and right upper extremities. In preferred embodiments, signals are then fed to a processing unit (904) carrying out "on-chip"

logic that then generates Composite Pulse Data Sets from raw signal. The Composite Pulse Data Sets are then communicated via either wireless or direct cable connection to an "off-device" display/computing unit (905) that provides the user with the final end-pulse oxygenation, arterial mainpulse oxygenation, and resulting venous saturation estimation with more graphical options (such as changes over time). There is also on-device storage (906) for code as well as buffering and packetized transfer of data. In an alternate embodiment, the processing unit simply coordinates communication of raw ECG and PPG signal data to the external computing/display device which handles all aspects of the hydration level estimation logic. In yet another embodiment, all aspects of hydration level estimation are carried out by the processing unit, including rendering of graphics and reporting of oxygen saturation. In this case, the external computing/display device provides only the display function.

FIGS. 10A-D show various view of the PPG collection device. 1001 shows the optical waveguide (in front of LEDs and detector); 1002 shows optional incorporated EKG electrodes; 1003 shows plug-in connector sites for EKG lead wires to adhesive EKG electrodes (on right and left chest).

FIG. 11 shows detail of the PPG head, with an optical waveguide (1101) that abuts the LEDs and detector (1102) on the interior of the device. The optical waveguide allows for collection of PPG signals at sites other than the finger.

Figure 12A:
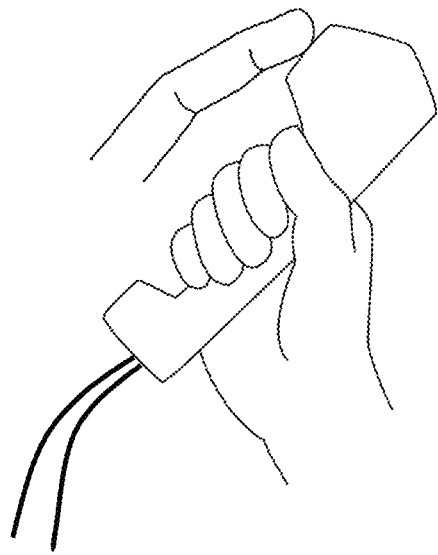
FIG. 12A is an illustration of the system of FIGS. 10A to 11 collecting PPG signals from a person's fingers.
Figure 12B:
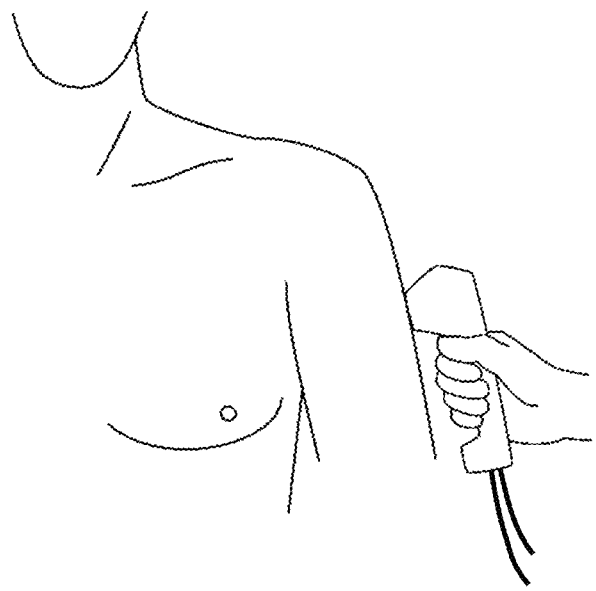
FIG. 12B is an illustration of the system of FIGS. 10A to 11 collecting PPG signals from the outside of a person's arm.

FIGS. 12A and 12B depict the device in use collecting PPG signals from the finger (FIG. 12A), and the outside of the upper arm (FIG. 12B). The PPG measurement end of the device is applied to the skin in a stable fashion so that PPG measurement can be taken over the course of 1-2 minutes or more. EKG electrodes are applied to the left and right sides of the torso (or upper extremities) and connected to the plug-ins on the smaller end of the device.

Figure 1:
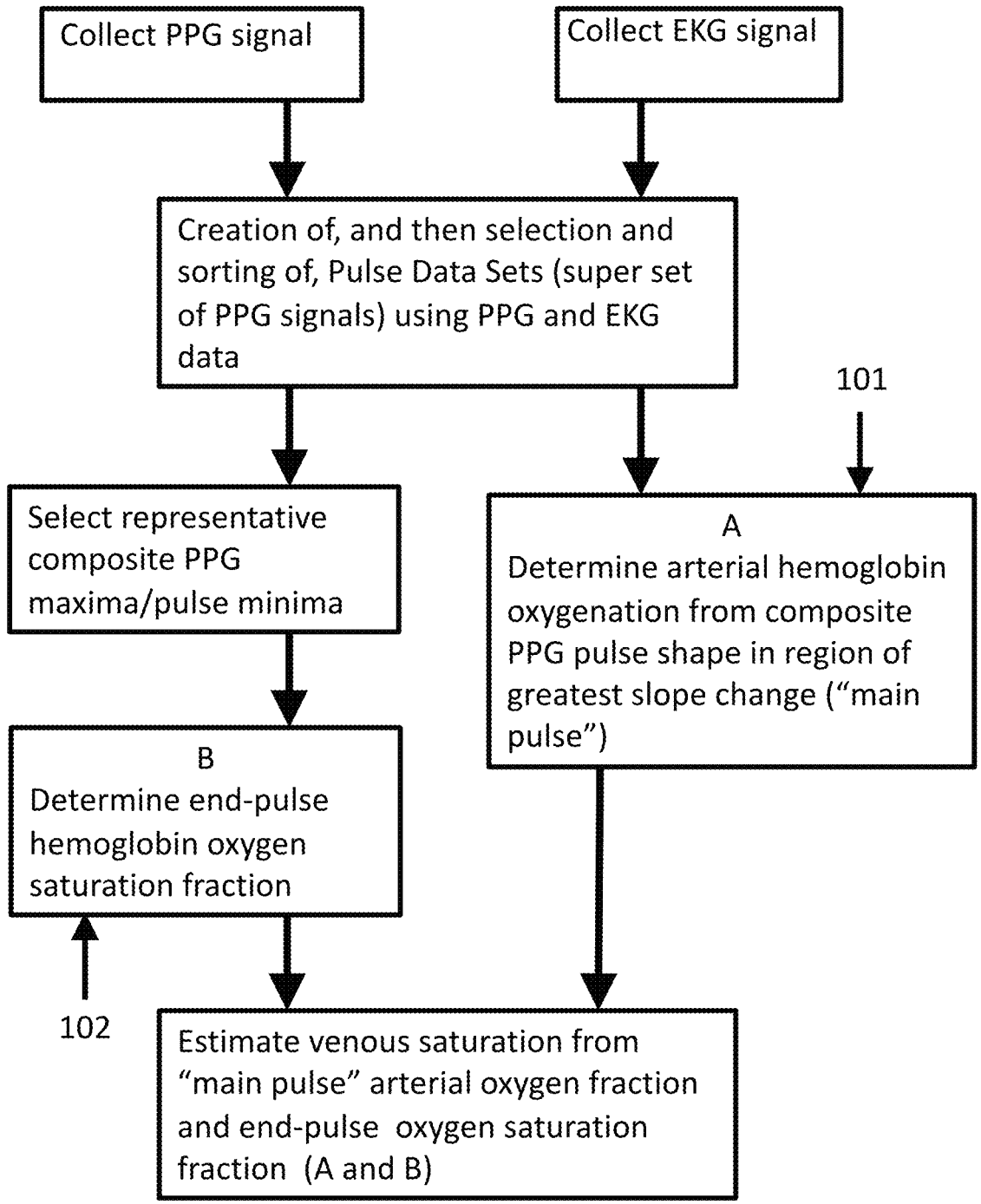
FIG. 1 is a top-level flow diagram of the operation of the present system.

Returning to FIG. 1, PPG and EKG signals are collected. PPG waveform selection is performed to screen out aberrant beats considerably different than the majority of pulses, such as premature ventricular contraction beats, an example where the cardiac contraction does change appreciably from the beat prior.

Figure 13:
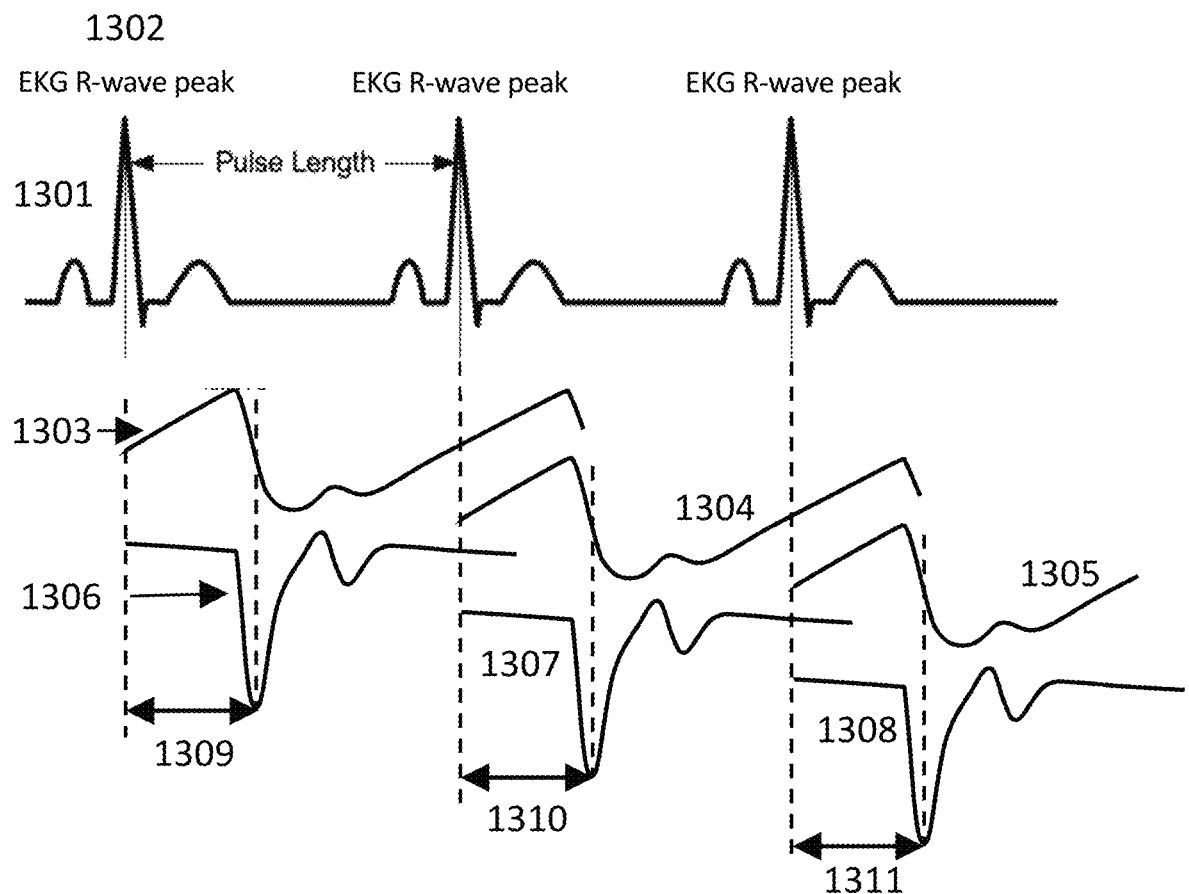
FIG. 13 is a is an illustration of EKG and PPG signals measured over time and generated SPOS signals corresponding thereto.

FIG. 13 shows: EKG signal (1301); EKG R-wave peak (1302); PPG signal segments (contained within Pulse Data Sets) (1303, 1304, 1305); SPOS signals (contained within Pulse Data Sets) (1306, 1307, 1308); PWTT using SPOS (also contained within Pulse Data Sets) (1309, 1310, 1311). This demonstrates selection of one of the PPG signals (in the current implementation red, infrared, and green are used, though the approach is not limited to using these alone) with full time length for both PPG signal and SPOS longer than the R-to-R duration.

The present method and system of intelligent pulse averaging counters the effect of drift in "K" (seen in equation 1), related to absorption from fixed elements in the tissue being analyzed. With averaging, some pulses will have an upward drift in K, some will have a downward drift, leaving the averaged pulse with more options for data point comparisons across the composite pulse width.

SPOS generates similar shaped curves for the LED signals for the different wavelengths, magnitude differing only by a multiplier that is the $\Sigma(\alpha * Hb)$ for the specific wavelength. The present system includes the two novel approaches of examining the SPOS signal in the region of the "negative spike" to determine:

the linearity of the rising LED SPOS signal, or
the fit of the SPOS signal to a combination of Gaussian derivatives and/or exponential and/or polynomial equations.

Given the similar shapes for the SPOS curves, any such fitting can be applied to one wavelength to yield a fitted curve. Fitting to another wavelength only requires finding the magnitude needed to best fit that curve. For example, if f(t) best fits the infrared LED SPOS, then "A" needed to best fit A*f(t) to the SPOS for the red LED signal yields the arterial oxygen saturation just as with the equation 1. The difference with the standard formulation is that this fitting is based on many more time points (up to 50 at slower heart rates) than the two (maximum and minimum) used in the standard formulation.

Figure 14:
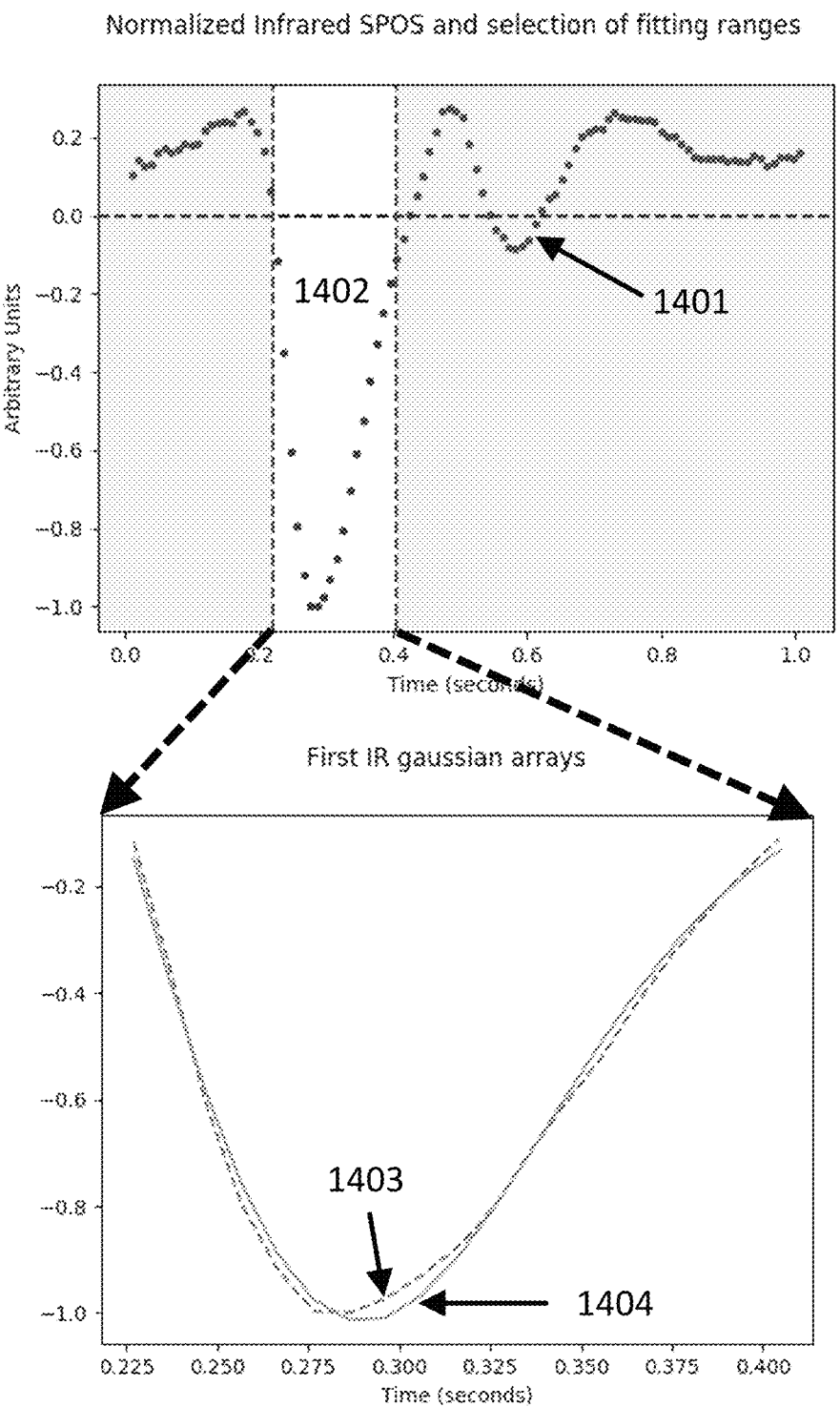
FIG. 14 is a is an illustration of one-sided Gaussian fitting.

FIG. 14 shows this concept using a one-sided Gaussian derivative fitting. Curve 1401 are the datapoints of a collected Composite IR SPOS signal with a fitting window 1402 selecting out the negative SPOS "spike". Curve 1403 shows the datapoints for the window in an expanded plot, also showing the one-sided Gaussian derivative fitted curve 1404.

The interval of the fitting window selected (the SPOS "negative spike"), or subset thereof (e.g. the rising SPOS right half of the "negative spike") represents a unique period wherein a single dominant and coherent physiologic event— the contraction of the left ventricle during the time of an open aortic valve—is clearly separate from other confounding physiologic features. This allows for extraction of parameters, which can then be applied to the entire PPG sensor pulse waveform.

Figure 2:
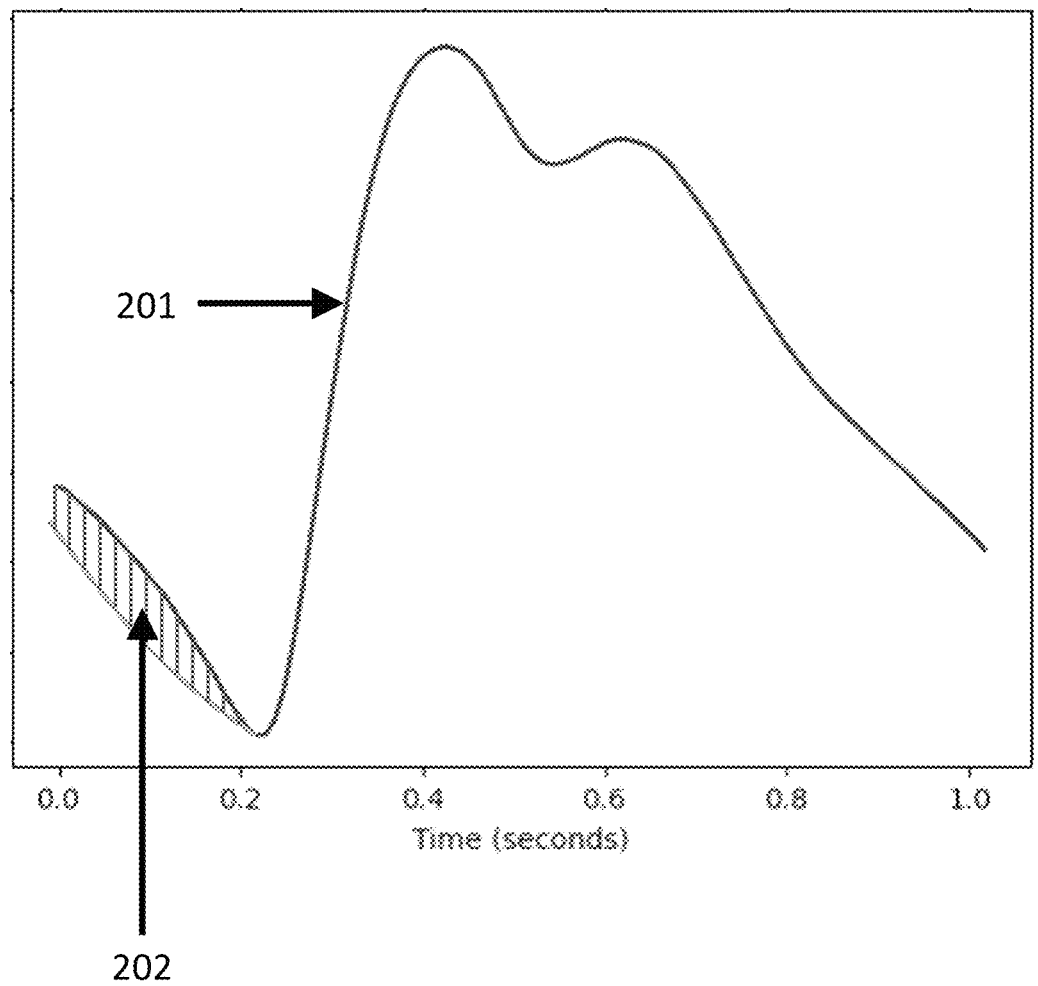
FIG. 2 shows a PPG signal filtered through a "tissue sandwich", showing slight changes at the end of the pulse.
Figure 3A:
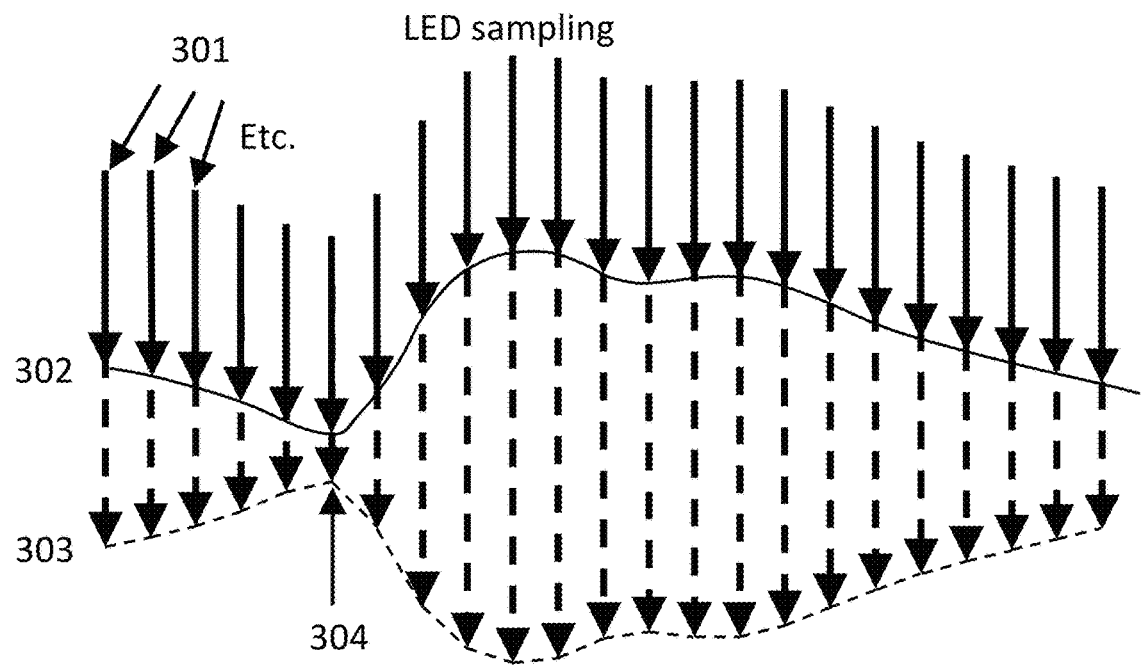
FIG. 3A is an illustration of LED sampling for standard PPG arterial hemoglobin oximetry.
Figure 3B:
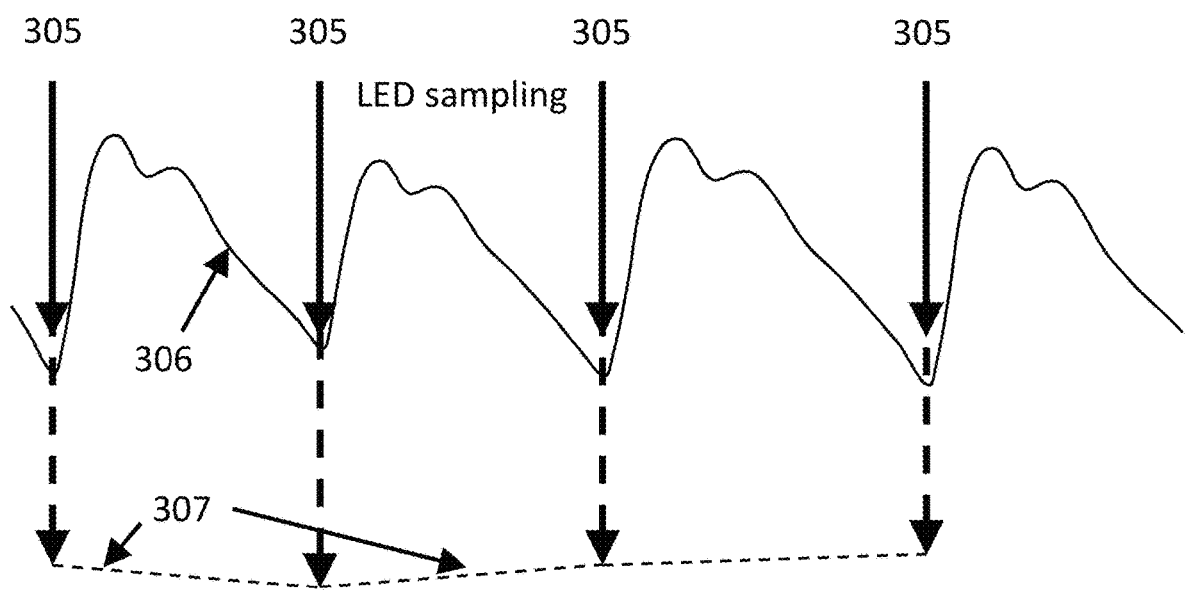
FIG. 3B is an illustration of end-pulse/signal maxima sampling.
Figure 4A:
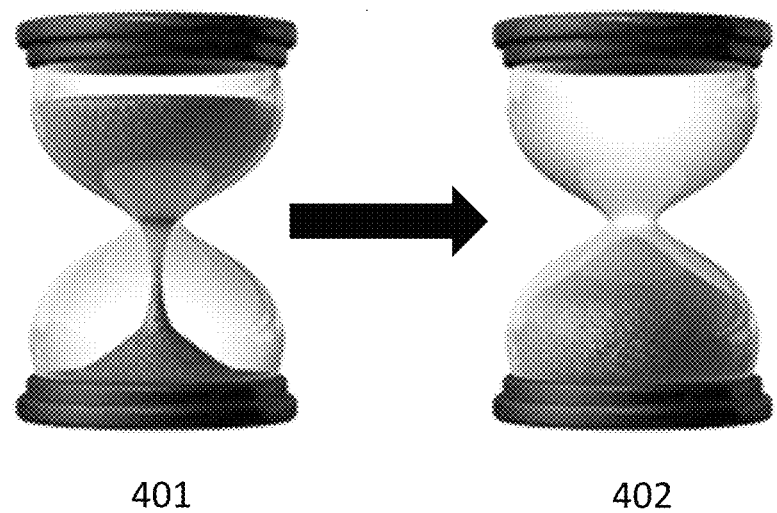
FIG. 4A illustrates arteriole/capillary/venule structure is shown as an hourglass.
Figure 4B:
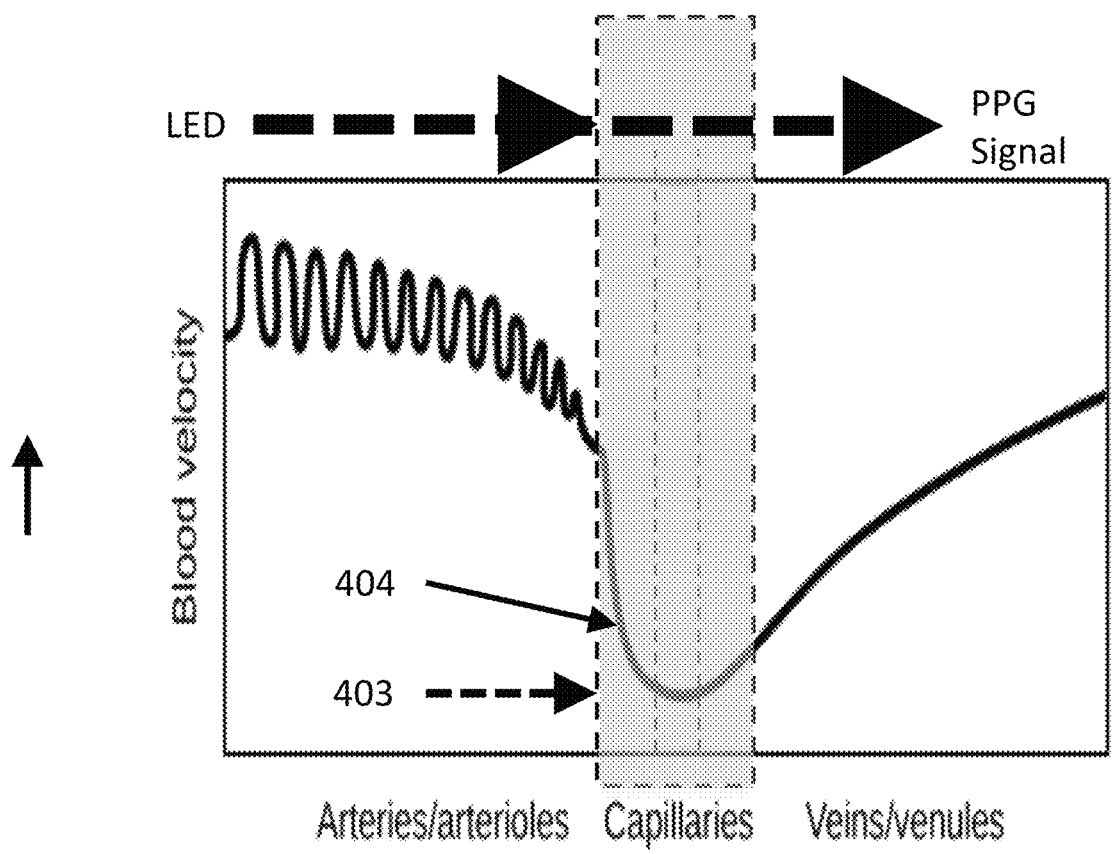
FIG. 4B corresponds to FIG. 4A, with the structure measured in reflective oximetry.
Figure 5A:
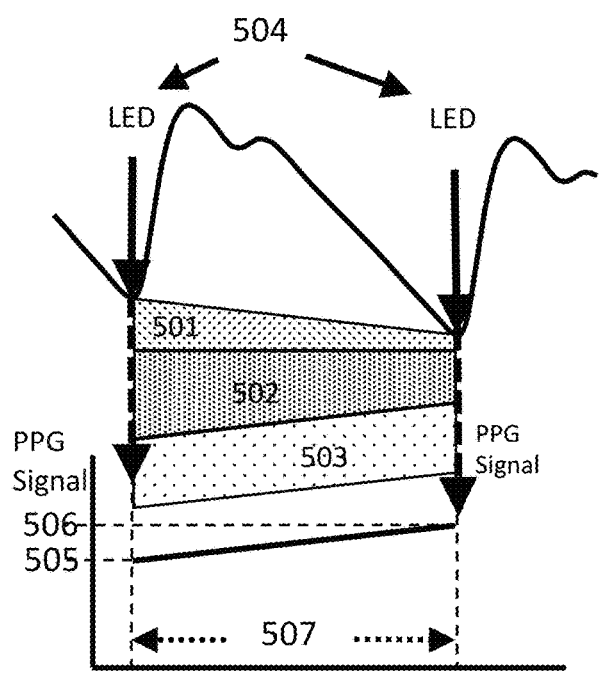
FIG. 5A illustrates LED sampling through the structure of FIGS. 4A and 4B at end-pulse/signal maxima before and after long pulses.
Figure 5B:
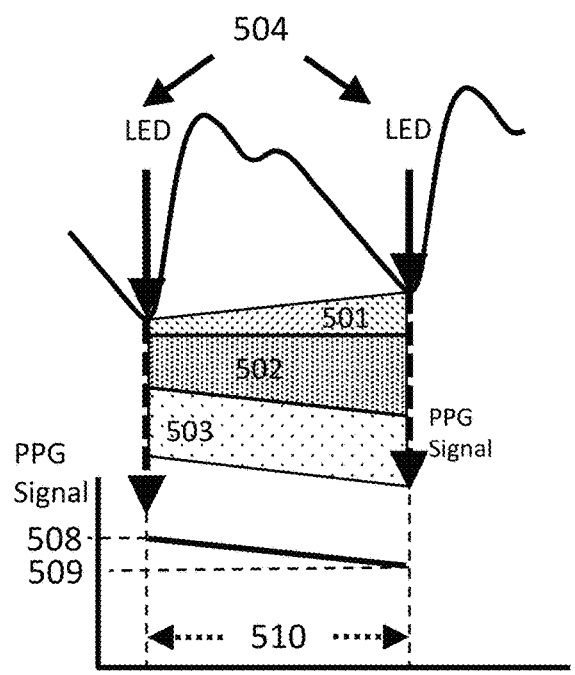
FIG. 5B illustrates LED sampling through the structure of FIGS. 4A and 4B at end-pulse/signal maxima before and after short pulses.
Figure 15:
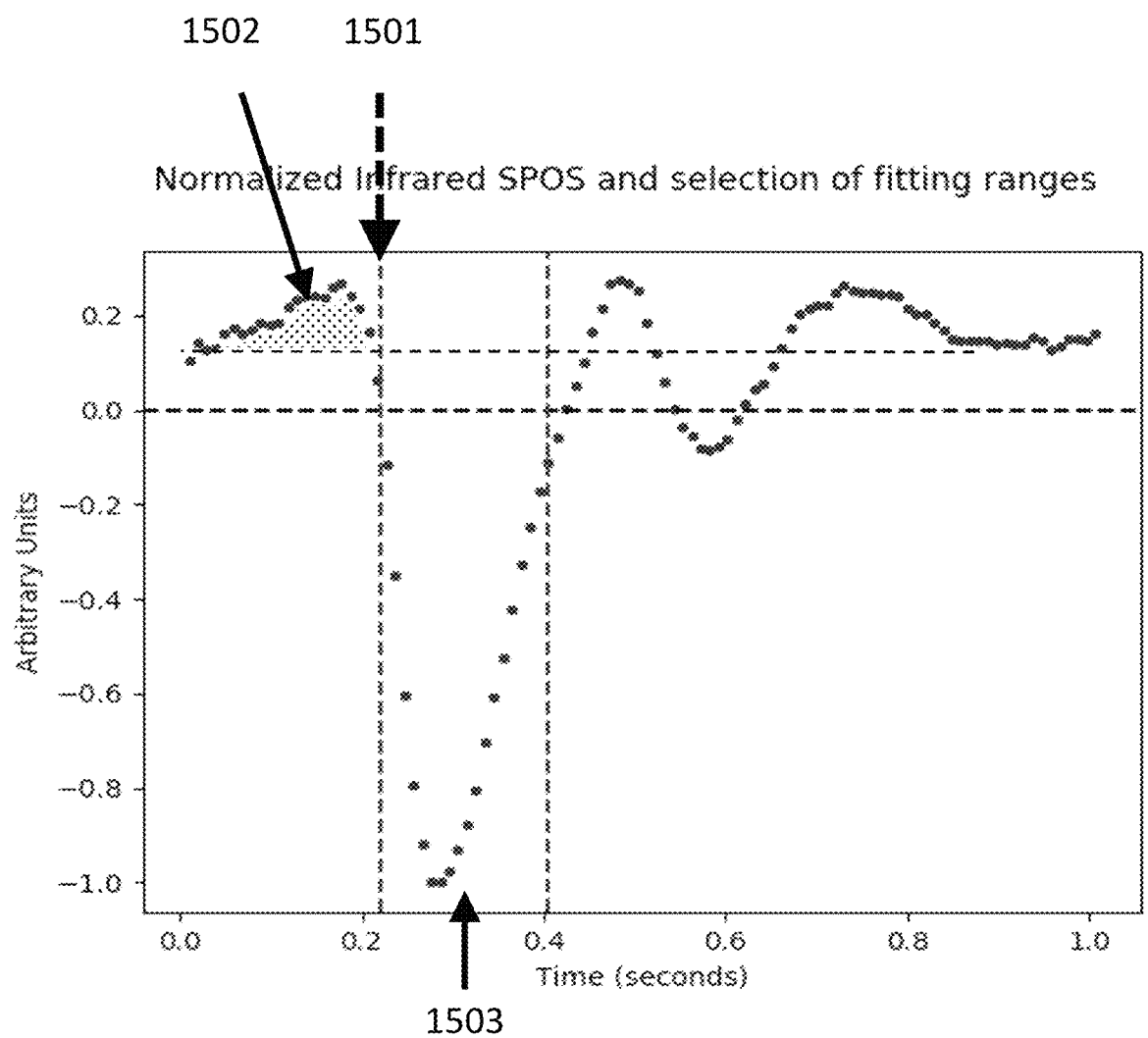
FIG. 15 illustrates the time relationship of the end-pulse/pre-pulse area of interest relative to the SPOS negative spike fitting window.
Figure 16:
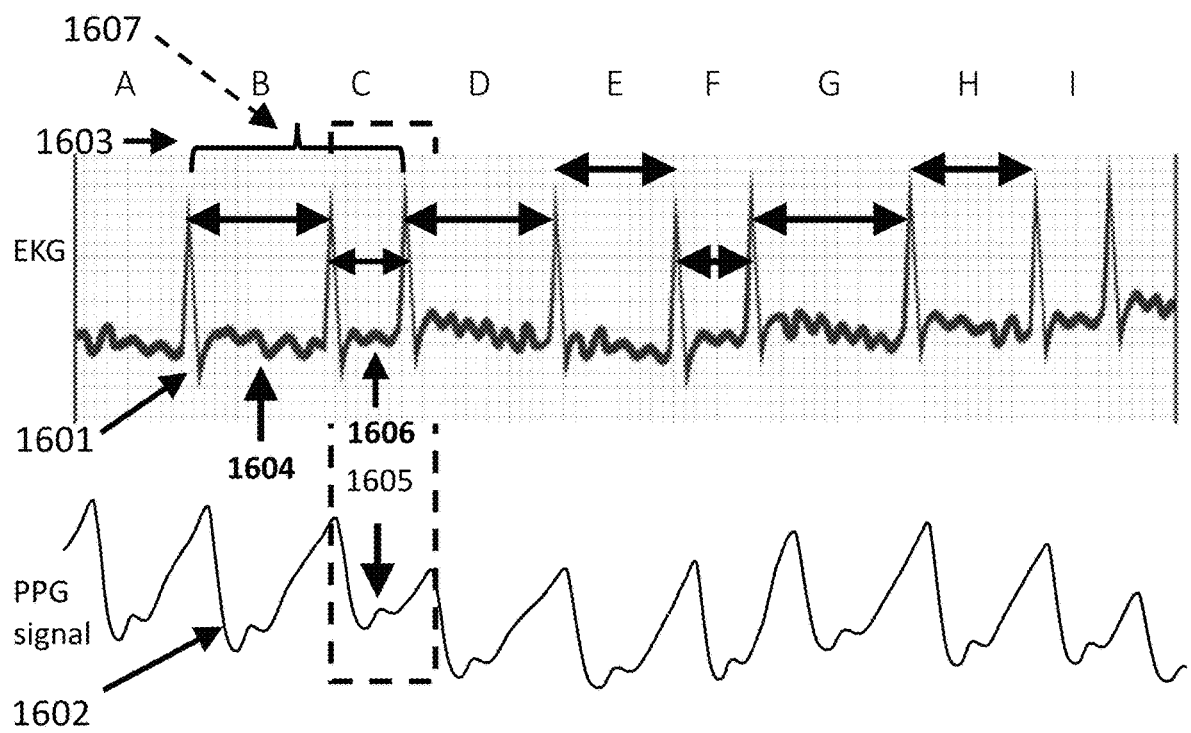
FIG. 16 illustrates a time-correlated comparison of EKG and PPG signals showing the relationships in creation of two-beat dependencies, showing current and prior "R-to-R".

The interval just preceding this fitting window for the "negative spike" of the SPOS represents yet another unique interval, as described in the summary of the physiology above. FIG. 15 shows the time relationship of the end-pulse/ pre-pulse area of interest relative to the SPOS negative spike fitting window. Time 1501 identifies the end-pulse point; region 1502 shows the excess SPOS PPG above expected linear or exponential "rolloff" (the shaded region of FIG. 15 corresponds to the shaded region of FIG. 2). Region 1503 identifies the window of the negative SPOS "spike" used to estimate arterial hemoglobin oxygen saturation fraction Two Beat Complex Creation for Venous Saturation Analysis:

2-beat complex selection for a longer train of pulses in atrial fibrillation (yielding random R-to-R duration) is shown in FIG. 16. Signal from a two-electrode, single lead EKG (curve 1601) is plotted in temporal alignment with an infrared (IR) LED PPG signal (curve 1602). As the infrared wavelength has relatively equivalent absorption from venous and arterial blood, this is the wavelength shown and used to select pulses for further analysis.

With accumulation of similar 2-beat complexes (based on similar n−1 R-to-R and n R-to-R duration), composite pulse construction can be taken from one pulse minima/signal maxima all the way through to the next pulse minima/signal maxima. With this formulation, pulse minima/signal maxima at the start of the pulse and at the end of the pulse can be compared, with additional information available regarding the cardiovascular state of the individual. FIG. 16 shows the top/bottom alignment of EKG (1601) and PPG signals (1602) showing the steps in the of generation of a composite PPG wave for purposes of venous oxygen saturation derivation.

The above EKG (1601) signal shows a series of pulses labeled A through I. Each of these pulses has a different duration, though some are closer in duration than others.

2-beat dependency ties together two successive beats, with key features being the R-to-R duration of the first beat, and the PPG signal of the second beat. This is a dependency (1603) as depicted in the bracket tying together the R-to-R duration of beat "B" (1604) and the PPG signal (1605) of beat "C". Additionally important in this analysis is the current R-to-R duration, which for this complex is the R-to-R duration of pulse "C" (1606). Notable with the bracketed complex 1603 is a paring of a long n−1 R-to-R followed by a short n R-to-R.

Pulses B and C are analyzed together, with the R-to-R duration of B and R-to-R duration of C putting this 2-beat complex in the long n−1 R-to-R/short n R-to-R "bin". Next, pulses C and D are considered together, with the R-to-R duration of C and R-to-R duration of D putting this 2-beat complex in the short n−1 R-to-R/long n R-to-R "bin". Next, pulses D and E are considered together, with the R-to-R duration of D and R-to-R duration of E putting this 2-beat complex in the long n−1 R-to-R/intermediate n R-to-R "bin". Next, pulses E and F are considered together, with the R-to-R duration of E and R-to-R duration of F putting this 2-beat complex in the intermediate n−1 R-to-R/short n R-to-R "bin". Next, pulses F and G are considered together, with the R-to-R duration of F and R-to-R duration of G putting this 2-beat complex in the short n−1 R-to-R/long n R-to-R "bin". Next, pulses G and H are considered together, with the R-to-R duration of G and R-to-R duration of H putting this 2-beat complex in the long n−1 R-to-R/intermediate n R-to-R "bin".

Figures 17A, 17B:
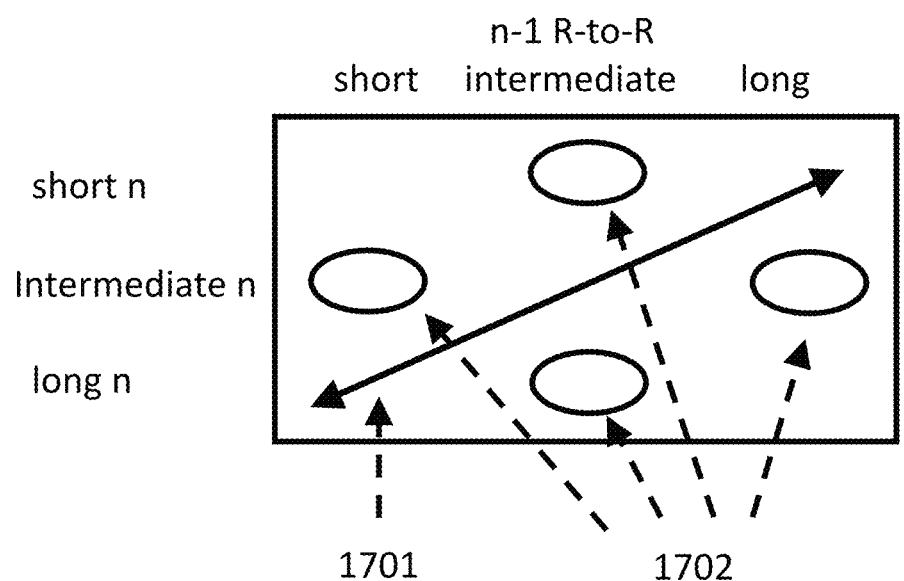
FIG. 17A illustrates the number of pulses in each bin for a run of a patient with normal sinus rhythm.
FIG. 17B illustrates filling of the Current R-to-R versus Prior R-to-R matrix for purposes of determining end-pulse oximetry (the greatest difference in R-to-R duration), and the "fall-back" or second tier bin choices using intermediate bins providing PPG signal maxima differences allowing for venous oxygen saturation estimation.

As this analysis reveals, atrial fibrillation provides a wide range of permutations of n−1 R-to-R and n R-to-R duration. This allows for analysis using short-long and long-short n−1 and n R-to-R durations, the combinations that reveals the biggest changes in PPG signal maxima. However, with normal sinus rhythm, it is harder to select combinations that will help reveal signal maxima differences. FIG. 17A shows the number of pulses in each bin for a run of a patient with normal sinus rhythm. Note how the diagonal corresponding to the same n−1 and n R-to-R durations are most populated and the short-long and long-short bins are the least populated. FIG. 17B shows the preferential filling of the Current R-to-R versus Prior R-to-R matrix (1701) for purposes of determining end-pulse oximetry (the greatest difference in R-to-R duration), and the "fall-back" or second tier bin choices using intermediate bins (1702) providing PPG signal maxima differences allowing for venous oxygen saturation estimation.

Measuring Venous Oxygen Saturation

Figure 18:
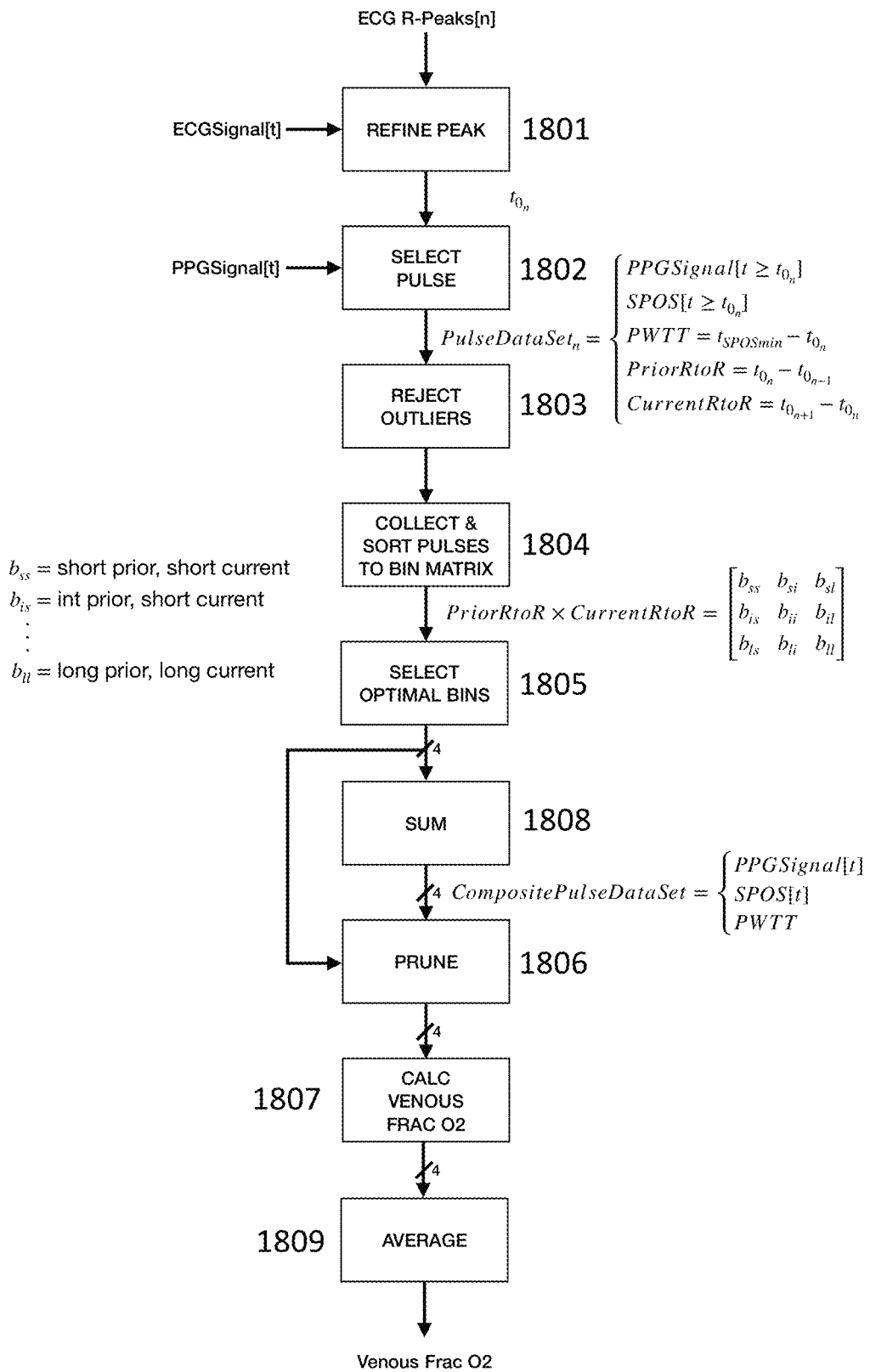
FIG. 18 is a top-level block diagram for the end-pulse/venous oxygen saturation calculation.

Because these 2-beat complexes define both the beginning and ending composite PPG signal, both first and second signal maxima (pulse minima) are therefore defined. And because accumulation of similar 2-beat complexes reduce the effect of DC drift, the methods described here also allow for an estimate of venous saturation. The top-level block diagram for the end-pulse/venous oxygen saturation calculation is seen in FIG. 18.

R-wave peak refinement of pulse "n" is done with curve fitting and interpolation (1801) prior to determining the prior (n−1) and current (n) R-to-R duration; then prior (n−1) and current (n) R-to-R durations for Pulse Data Set "n" are incorporated into Pulse Data Set "n" (1802). PPG signals are gathered, and a process of outlier rejection is carried out (including but not limited to data determined to be corrupted using accelerometer input, as well as cross-checking with multiple LED PPG sensors, 1803). Once the PPG signals of the current Pulse Data Set have been selected, the Pulse Data Set is considered together with all available prior Pulse Data Sets and their PPG signals (each of which is associated with a prior (n−1) R-to-R duration and current (n) R-to-R duration).

Available Pulse Data Sets are then sorted into a 3 by 3 bin matrix of Prior R-to-R and Current R-to-R, each of which are considered and deemed to be short, intermediate, or long duration (1804). Dynamic boundary adjustment is used to ensure relatively equal numbers across bins, to the extent possible: normal sinus rhythm yields few Pulse Data Sets available for bins off the diagonal of short-short, intermediate-intermediate, and long-long (see FIG. 17). After all Pulse Data Sets are allocated into bins, the optimal bins are selected, e.g. those bins containing the largest number of Pulse Data Sets and those that reveal the biggest changes in signal maxima (1805). With the optimal bins established, and initial Composite Pulse Data Set is formed by adding together the corresponding PPG signals of each wavelength for each Pulse Data Set in the bin (1808).

Figure 20:
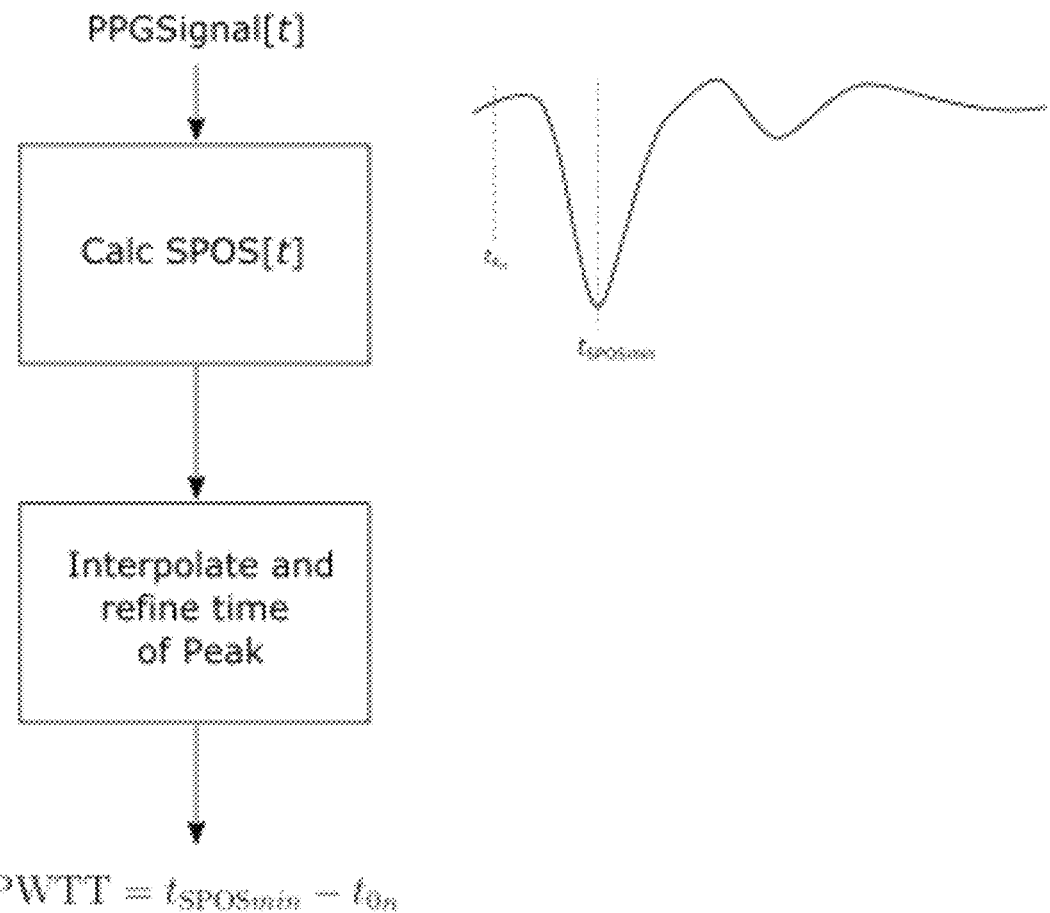
FIG. 20 illustrates the derivation of the Pulse Wave Transit Time (PWTT).

With the Pulse Data Sets in a bin and the initial Composite Pulse Data Set in hand, a pruning loop is carried out for each bin to weed out Pulse Data Sets with noisy or otherwise aberrant PPG signals (1806) that made it through the coarser outlier rejection. For each Pulse Data Set in the bin, and for each wavelength in the Pulse Data Set, the PWTT for the wavelength is compared against the PWTT for the wavelength for the Composite Pulse Data Set (aggregate of all the pulses). If the PWTT of two of the current three wavelengths (red, green, IR) are within 15% of the PWTT of the Composite Pulse Data Set, the Pulse Data Set is left in the composite. If not, the Pulse Data Set is rejected ("pruned") and the process is run again with the remaining Pulse Data Sets. A pruned Pulse Data Set is removed from the bin and subtracted from the Composite Pulse Data Set. If the number of Pulse Data Sets falls below a specified threshold for the number in the bin (good results have been obtained with numbers down to 4), then an additional Pulse Data Set is added prior to reporting any results. The algorithm is seen in FIG. 19. FIG. 20 shows the derivation of the Pulse Wave Transit Time (PWTT). This is done using the Signal Prime Over Signal (SPOS(t)) curve for each wavelength PPG signal(t), together with interpolation and (negative) peak refinement.

Figure 21:
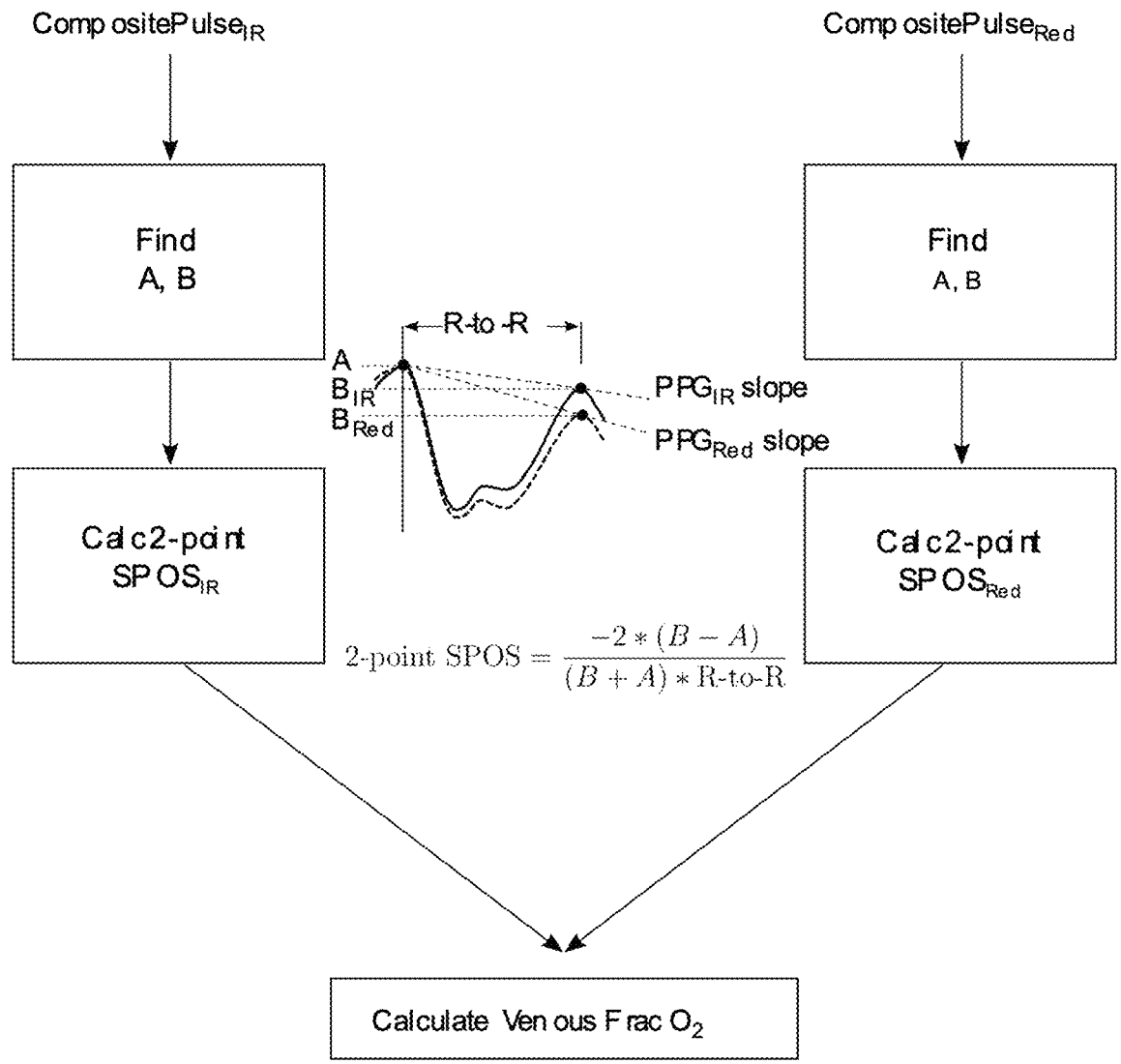
FIG. 21 shows the calculation of end-pulse/venous oxygen saturation.

The calculation of end-pulse/venous oxygen saturation then proceeds as shown in FIG. 21. The venous oxygen saturation calculation follows the derivation shown in Appendix B using 2-point composite signals composed of PPG signal maxima corresponding to incongruent R-to-R duration from 2-beat complexes (1807). The results are averaged and the venous fractional oxygen saturation is reported (1809).

Figure 22:
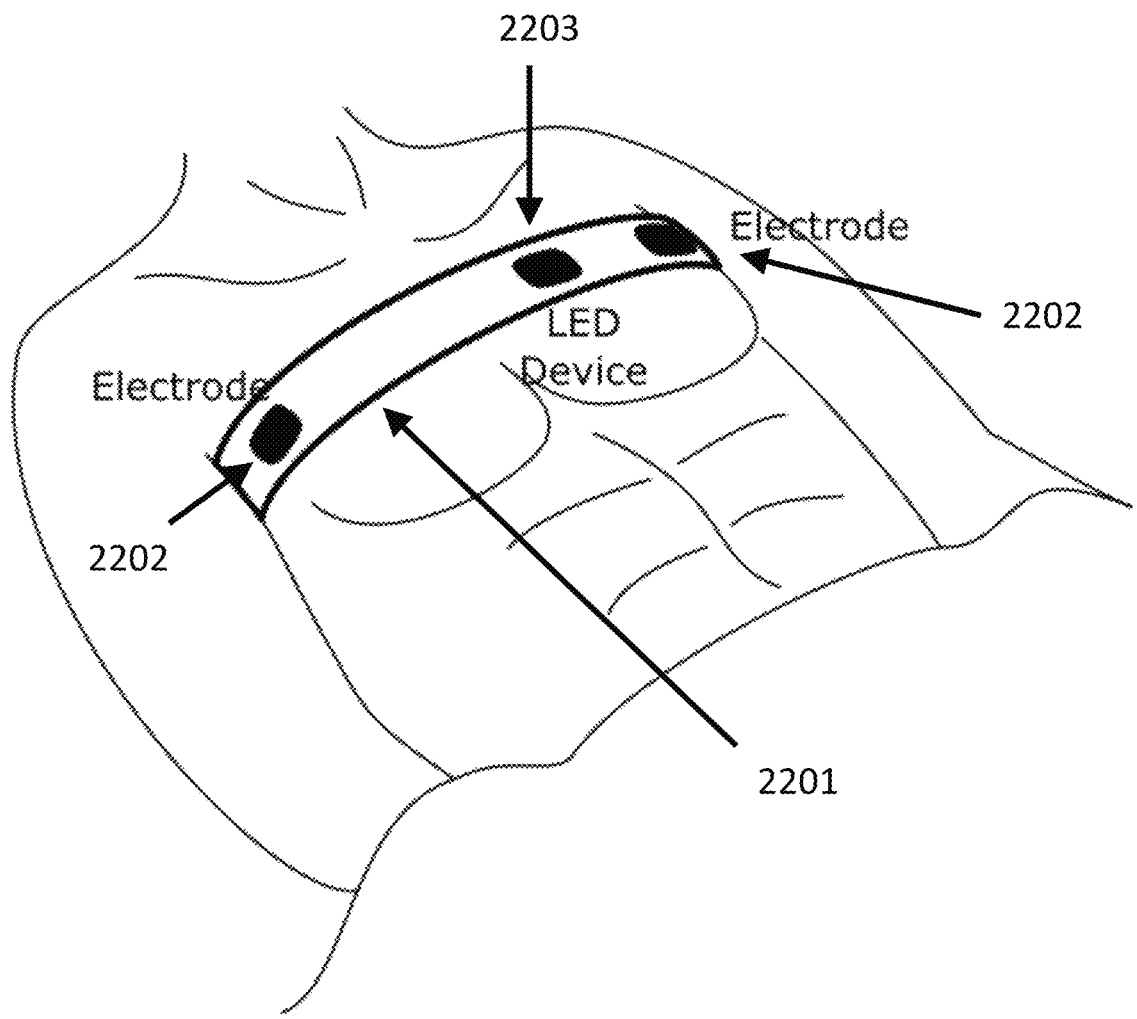
FIG. 22 illustrates an exemplary embodiment of the present system disposed in a chest strap.

System Operation:

Operational alternative options are presented in the various exemplary embodiments of the present system, below. It is to be understood that the present system can be embodied in any of the systems described herein, and that the present system is not limited solely to the various exemplary embodiments described below:

FIG. 22 illustrates use of a chest strap (2201) across the chest, with incorporated electrodes (2202) contacting the left and right chest, and LED device with detector (2203).

Figure 23:
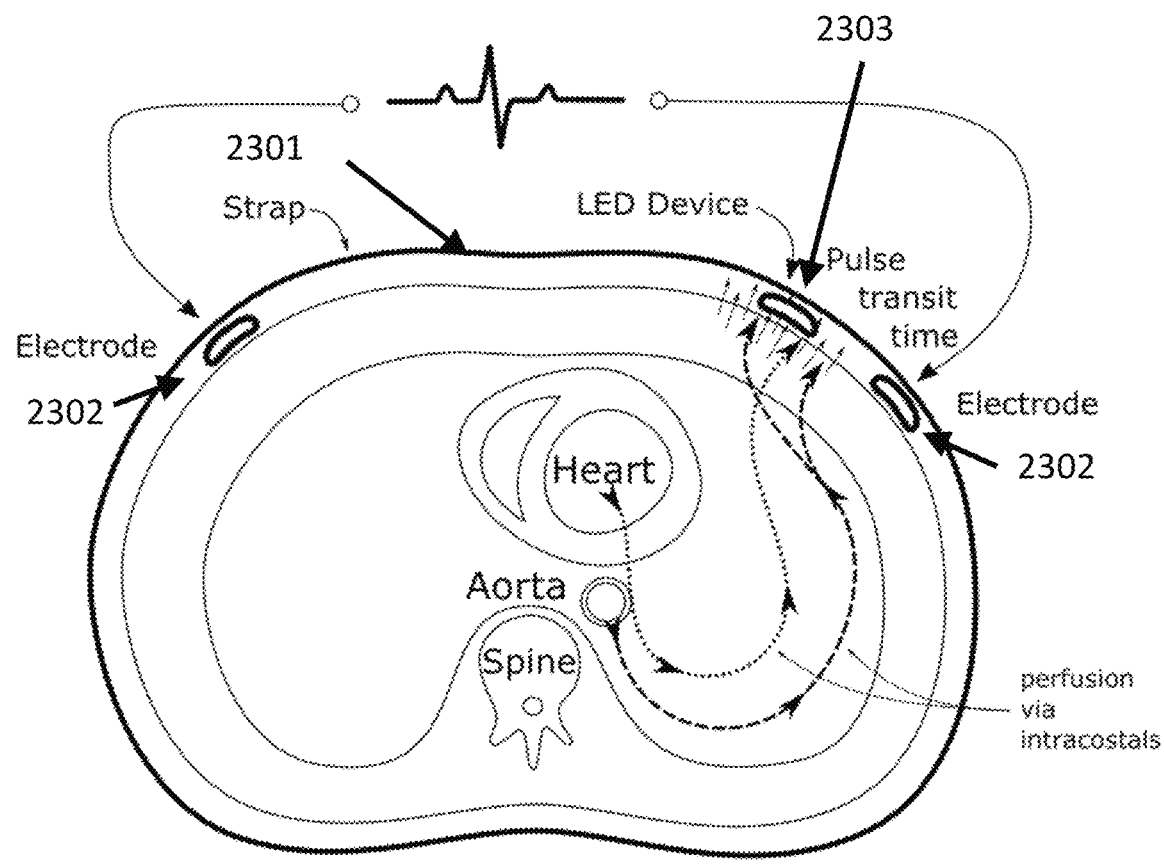
FIG. 23 is a is a sectional view through the patient corresponding to FIG. 22.

FIG. 23 illustrates cross section of a chest strap (2301) across the chest, with incorporated electrodes (2302) contacting the left and right chest, and LED device with detector (2303).

Figure 24:
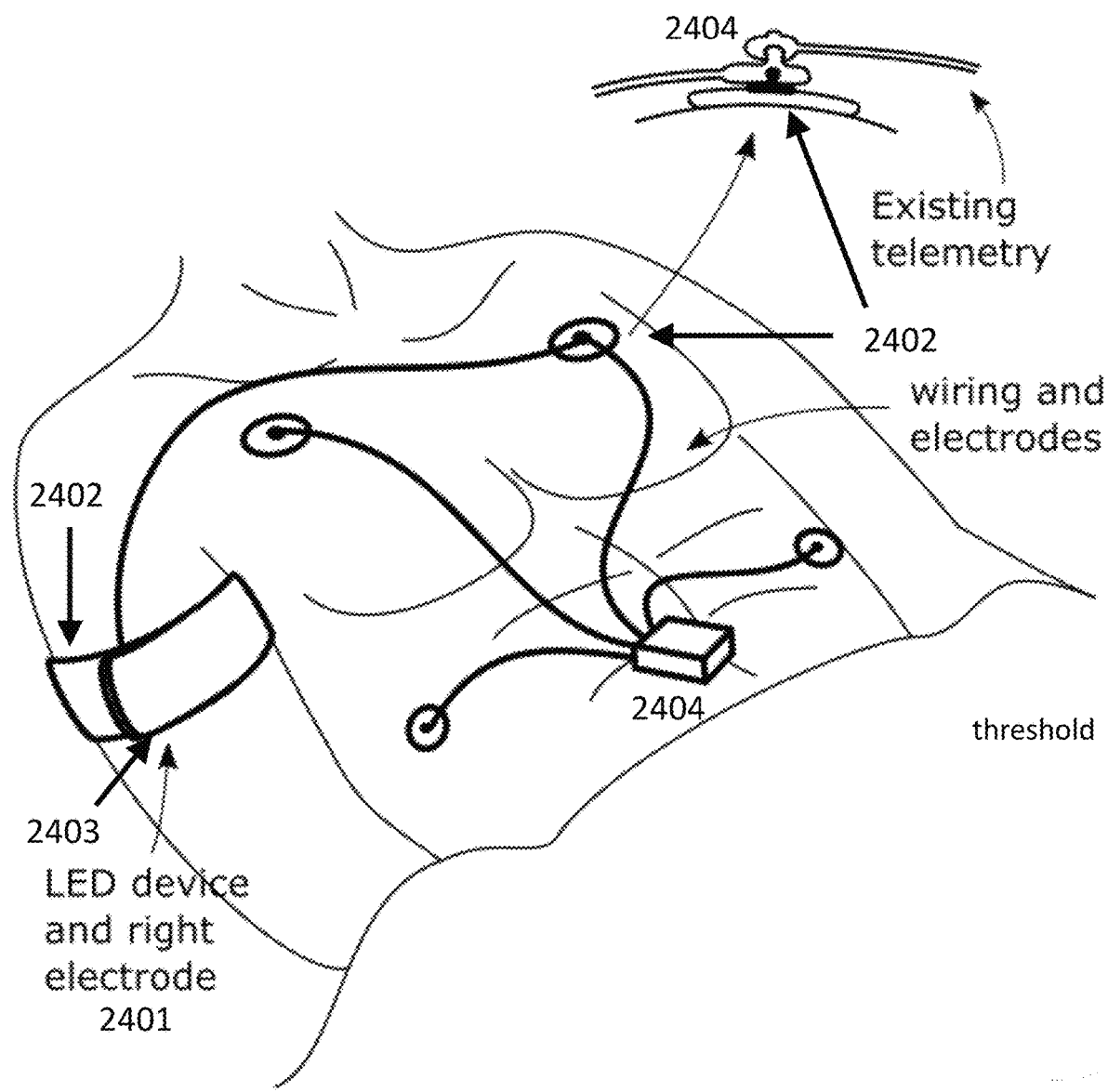
FIG. 24 illustrates an exemplary embodiment of the present system incorporating a bicep strap with an electrode extending therefrom.

FIG. 24 illustrates use of a bicep strap (2401), with incorporated electrode (2402) and LED device with detector (2403). A second electrode piggybacks off existing telemetry wiring (2404).

Figure 25:
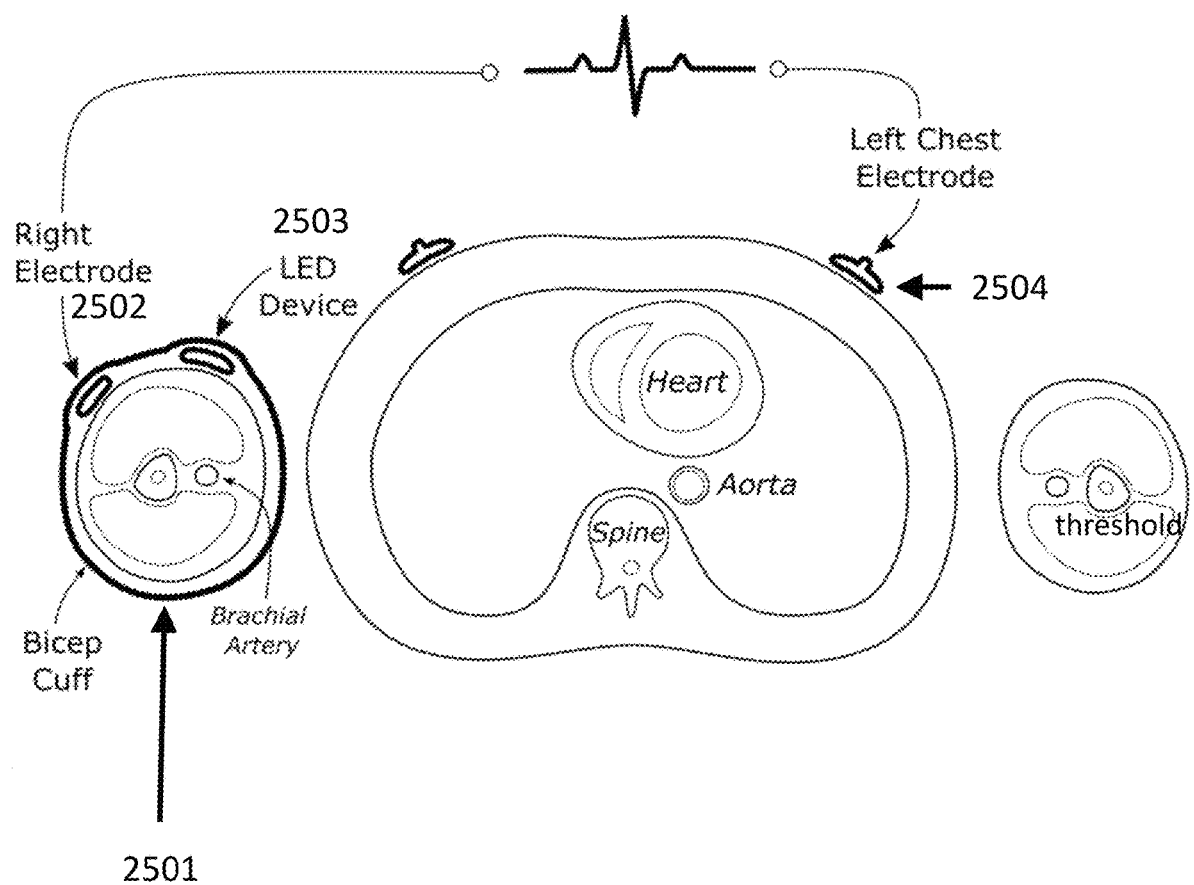
FIG. 25 is a is a sectional view through the patient corresponding to FIG. 24.

FIG. 25 illustrates cross section of a bicep strap (2501), with incorporated electrode (2502) and LED device with detector (2503). A second electrode piggybacks off existing telemetry wiring (2504).

An advantage of a chest or arm strap or band is that the band/strap provides a normal force on the LED of the PPG sensor to get a good signal off the chest wall. In aspects where a chest or arm strap is used, optional "traction" may also be provided on the inside of the strap, similar to the silicone/adhesive bead that is found on the inside of standard bike shorts to keep the legs from riding up.

APPENDIX A: CARDIOVASCULAR PHYSIOLOGY BACKGROUND

In normal health, delivery of oxygen and glucose to tissues is adequate for tissues to meet their energy needs by aerobic glycolysis, a process using oxygen to breakdown glucose that releases far more energy than anaerobic glycolysis, or fermentation (metabolism of glucose without oxygen). Whereas aerobic glycolysis breaks down glucose to water and carbon dioxide, anaerobic glycolysis breaks the glucose down to lactic acid. In health lactate is low, and pH (affected by the presence of lactic acid) is maintained around 7.4. Anaerobic metabolism with production of lactic acid allows muscles to transiently access extra energy when the tissue needs are high and there is insufficient delivery of oxygen to "burn" the available glucose (such a situation seen when sprinting at maximal effort for short distances). The lactate thus produced is then cleared from the blood stream by the liver and converted back to glucose once the physiologic stress is resolved. This allows for complete aerobic glycolysis of the previously fermented glucose.

However, when that physiologic stress is sustained rather than transient, many things begin to go awry. This can happen when infection causes the metabolism to drastically increase; or it can happen when delivery capability is suddenly reduced, as with a heart attack; it can also happen in the setting of otherwise moderate stress in the setting of baseline reduction in heart pump function. In all cases, the oxygen requirements of the tissues increase relative to what the cardiovascular system can deliver. Oxygen obtained in the lungs cannot fully replace the oxygen removed from the blood stream in the capillaries. In this situation the arterial hemoglobin oxygenation will fall—though the venous saturation will fall even more due to the body eating into the oxygen reserve in the venous blood stored up prior to the stress (oxygen saturation of venous blood may exceed 80% in unstressed normal health). All of which yields a growing difference between arterial and venous oxygen.

As venous oxygenation falls further, lactate levels will eventually begin to rise, though recent studies have shown that the rising in lactate is preceded by a measurable fall in venous oxygenation, which that fall providing clinically useful information. To measure the venous blood oxygen, though, requires a venous blood gas sample. This is obtained by a blood draw that is immediately placed on ice and sent to a qualified lab. All of which is a relatively expensive and invasive procedure with a minimum turn-around time of around 10-15 minutes, if done STAT.

Circulatory shock causes inadequate oxygen delivery, resulting in mitochondrial hypoxia. With failure of mitochondrial oxidative phosphorylation, energy metabolism becomes dependent on anaerobic glycolysis. Anaerobic glycolysis sharply increases the production of cellular lactate, and then blood levels. With severe infection, the blood lactate concentration varies in proportion to the ongoing deficit in tissue oxygenation. The ability of the patient to clear blood lactate indicates restoration of oxygen delivery with resuscitation. Studies have shown that a lactate clearance of 10% or more predicts survival from septic shock.

Studies have also shown that falling venous oxygen can provide earlier usable information than rising lactate. This unfortunately requiring ongoing invasive monitoring via a central venous line (or Swan-Ganz intracardiac catheter) and/or repeated blood draws.

APPENDIX B: VENOUS HEMOGLOBIN SATURATION CALCULATION

At the pulse minima (LED signal maxima), $$\text{Signal}_{max} = K \cdot I_O \cdot e^{[-(\alpha \cdot thickness)_{connectivetissue}]} \cdot e^{[-(staticarterialblood) \cdot \Sigma(\alpha \cdot Hb)_{arterial}]} \quad (1)$$

$$\text{Signal} = K \cdot e^{[-ArterialPulse(t) \cdot \Sigma(\alpha \cdot Hb)_{arterial}]} \cdot e^{[-VenousPulse(t) \cdot \Sigma(\alpha \cdot Hb)_{venous}]} \quad (2)$$

where $(\alpha \cdot Hb)_{arterial}$ and $(\alpha \cdot Hb)_{venous}$ are the absorption coefficients of the type of hemoglobin (deoxyhemoglobin, oxyhemoglobin, carboxyhemoglobin, methemoglobin), and $\Sigma(\alpha \cdot Hb)_{arterial}$ and $\Sigma(\alpha \cdot Hb)_{venous}$ are summations of absorption coefficient for each type of hemoglobin times the fraction of each type of hemoglobin making up the arterial and venous pulses (as they have different compositions, the arterial blood carrying a much higher fraction of oxygenated blood).

Collecting the LED signal maxima (A and B, separated in time by R-to-R duration), treating them as the time varying signal, and reordering the equation:

$$\text{Signal}_{max}(t) = K \cdot I_O \cdot e^{[-(\alpha \cdot thickness)_{connectivetissue}]} \cdot e^{[-(staticarterialblood) \cdot \Sigma(\alpha \cdot Hb)_{arterial}]} \cdot e^{[-(dynamicarterialblood) \cdot \Sigma(\alpha \cdot Hb)_{arterial}]} \cdot e^{[-(venous(t)) \cdot \Sigma(\alpha \cdot Hb)_{venous}]} \quad (3)$$

With arteriole blood priming an "hour glass" structure consisting of the arterioles, capillaries, and venules toward the end of the pulse, some change in the composition of the blood toward the end of the pulse is present. This suggests that a re-evaluation of the assumption of flat venous blood profile can be done by using the following to model the change in blood composition at PPG signal maxima:

delta arterial blood = gamma * delta volume  (4)

delta venous blood = (1−gamma) * delta volume  (5)

Where gamma is somewhere between 1 and 0.5.

$$\text{Signal}_{max}(t) = \quad (6)$$
$$K_v \cdot e^{[-((1-gamma) \cdot volume(t)) \cdot \Sigma(\alpha \cdot Hb)_{arterial}]} \cdot e^{[-(gamma \cdot volume(t)) \cdot \Sigma(\alpha \cdot Hb)_{venous}]}$$

$$2ptSPOS(\text{Signal}_{max}(t)) = -\left(\frac{B-A}{R-to-R}\right) \cdot \left(\frac{2}{B+A}\right) \quad (7)$$

$$2ptSPOS(\text{Signal}_{max}) = -\left(\frac{dVolume(t)}{2 \cdot dt}\right) \cdot \quad (8)$$
$$\left[gamma \cdot \sum(\alpha \cdot Hb)_{arterial} + (1-gamma) \cdot \sum(\alpha \cdot Hb)_{venous}\right]$$

$$2ptSPOS(\text{Signal}_{max}) / \left[gamma \cdot \sum(\alpha \cdot Hb)_{arterial} + (1-gamma) \cdot \sum(\alpha \cdot Hb)_{venous}\right] = -\left(\frac{dVolume(t)}{2 \cdot dt}\right) \quad (9)$$

Once again assuming that there is only deoxyhemoglobin (Hb) and oxyhemoglobin (HbO2), $$\frac{2ptSPOS(Signal_{max}(t))}{[\text{gamma} * \sum (\alpha * Hb)_{arterial} + (1 - \text{gamma}) * (\alpha_{Hb} + (\alpha_{HbO_2} - \alpha_{Hb}) * HbO_2)]} = -\left(\frac{dVolume(t)}{2 * dt}\right) \quad (10)$$

Done at two or more different wavelengths (e.g. red, infrared, though not exclusive to these), one can solve for HbO2, given that the only unknowns are HbO2 and dVolume(t)/dt. Note that $\Sigma(\alpha*Hb)_{arterial}$ at each wavelength is known from analyses done elsewhere in the system description.

$$\text{With } R = \frac{(2ptSPOS(Signal_{maxRed}(t)))}{(2ptSPOS(Signal_{maxIR}(t)))} \quad (11)$$

$$HbO_2 = \frac{(1 - \text{gamma}) * [-\alpha_{IR_{Hb}} * R - \alpha_{Red_{Hb}}] + \text{gamma} * [-\sum(\alpha * Hb)_{arterialIR} * R + \sum(\alpha * Hb)_{arterialRed}]}{(1 - \text{gamma})[R * (\alpha_{IR_{HbO_2}} - \alpha_{IR_{Hb}}) + (\alpha_{Red_{Hb}} - \alpha_{Red_{HbO_2}})]} \quad (12)$$

What is claimed is:

1. A system for determining venous oxygen saturation, comprising:
   (a) a device positionable against skin of a person;
   (b) at least one PPG sensor mounted on the device for measuring a PPG signal of the person at multiple wavelengths of light;
   (c) a plurality of electrodes for measuring an EKG signal of the person;
   (d) a computer logic system for receiving and analyzing the PPG signal and the EKG signal,
   wherein the computer logic is configured to:
      identify cardiac cycles in the EKG signal;
      segment the PPG signal into a series of PPG signal segments based upon features in the identified cardiac cycles,
      sort the PPG signal segments into a plurality of bins based upon a similarity in durations of prior R-to-R cardiac cycles and a similarity in durations of current R-to-R cardiac cycles,
      generate a composite signal for each of the plurality of bins,
      generate a composite Signal Prime Over Signal (SPOS) for each of the composite signals by calculating a derivative of the composite signal and normalizing the derivative of the composite signal by the composite signal itself,
      measure venous oxygen saturation of the person by:
         (a) calculating arterial oxygen saturation by comparing the composite SPOS signals measured at different wavelengths of light,
         (b) sub-sampling composite signals at two consecutive signal maxima measured at different wavelengths of light, and
         (c) comparing the sub-sampled composite SPOS signals measured at different wavelengths of light to the calculated arterial oxygen saturation to determine venous oxygen saturation, and
      output to a display device an indication of the determined venous oxygen saturation to enable noninvasive monitoring of cardiac conditions.

2. The system of claim 1, wherein to measure venous oxygen saturation of the person, the computer logic system is configured to select preferred bins from which the composite signals are used when determining the venous oxygen saturation.

3. The system of claim 2, wherein the preferred bins correspond to the bins having the largest number of PPG signal segments therein.

4. The system of claim 3, wherein the preferred bins correspond to the bins having the largest difference between current and prior R-to-R values.

5. The system of claim 1, wherein to generate the composite signal for each of the plurality of bins, the computer logic system is configured to sum or average the PPG signal segments in the bin.

6. The system of claim 1, wherein to generate the composite signal for each of the plurality of bins, the computer logic system is configured to remove aberrant PPG signal segments from the calculation of the composite signal.

7. The system of claim 6, wherein to remove aberrant PPG signal segments from the calculation of the composite signal, the computer logic system is configured to iteratively recalculate the composite signal, by:
   comparing a SPOS of each of the PPG signal segments used to calculate a composite signal against the SPOS of the calculated composite signal,
   removing outlier PPG signal segments,
   re-calculating the composite signal with the outlier PPG signal segments removed, and repeating the iteration until there are no more outlier PPG signal segments.

8. The system of claim 1, wherein the device is a hand-held device with the at least one PPG sensor mounted thereon and a plurality of electrode wires extending therefrom.

9. The system of claim 8, wherein the device is a hand-held device with the at least one PPG sensor mounted thereon and at least one of the plurality of electrodes mounted thereon.

10. The system of claim 8, wherein an optical waveguide is interposed between the at least one PPG sensor on the device and the skin of the person.

11. The system of claim 1, wherein the device is positioned within a strap or band disposed around a chest or limb of the person such that the at least one PPG sensor and the plurality of electrodes are disposed within the strap or band disposed around the chest or limb of the person.

12. The system of claim 1, wherein the device is a patch with the at least one PPG sensor and at least one of the plurality of electrodes positioned therein.

13. The system of claim 1, wherein the computer logic system is positioned within the device such that the composite signals are generated within the device, and wherein the device comprises:
   a data transmission system for transmitting one or both of:
      the composite signals to a remote computer system for analysis, or measured PPG and EKG signals to a remote computer system for analysis.

14. A system for determining venous oxygen saturation, comprising:
   (a) a device positionable against skin of a person;
   (b) at least one PPG sensor mounted on the device for measuring a PPG signal of the person at multiple wavelengths of light;
   (c) a plurality of electrodes for measuring an EKG signal of the person;
   (d) a computer logic system for receiving and analyzing the PPG signal and the EKG signal, wherein the computer logic system is configured to:
identify cardiac cycles in the EKG signal;
segment the PPG signal into a series of PPG signal segments based upon features in the identified cardiac cycles,
sort the PPG signal segments into a plurality of bins based upon a similarity in durations of prior R-to-R cardiac cycles and a similarity in durations of current R-to-R cardiac cycles,
generate a composite signal for each of the plurality of bins by summing or averaging the PPG signal segments in the bin, and
generate composite Signal Prime Over Signal (SPOS) for each of the composite signals by calculating a derivative of the composite signal and normalizing the derivative of the composite signal by the composite signal itself, and
measure venous oxygen saturation of the person by:
(a) calculating arterial oxygen saturation by comparing the composite SPOS signals measured at different wavelengths of light,
(b) sub-sampling composite signals at two consecutive signal maxima measured at different wavelengths of light, and
(c) comparing the sub-sampled composite signals measured at different wavelengths of light to the calculated arterial oxygen saturation to determine venous oxygen saturation.

15. A system for determining venous oxygen saturation, comprising:
(a) a device positionable against skin of a person;
(b) at least one PPG sensor mounted on the device for measuring a PPG signal of the person at multiple wavelengths of light;
(c) a plurality of electrodes for measuring an EKG signal of the person;
(d) a computer logic system for receiving and analyzing the PPG signal and the EKG signal,
wherein the computer logic system is configured to:
identify cardiac cycles in the EKG signal;
segment the PPG signal into a series of PPG signal segments based upon features in the identified cardiac cycles,
sort the PPG signal segments into a plurality of bins based upon a similarity in durations of prior R-to-R cardiac cycles and a similarity in durations of current R-to-R cardiac cycles,
generate a composite signal for each of the plurality of bins comprising a system for removing aberrant PPG signal segments from the calculation of the composite signal by iteratively re-calculating the composite signal, by:
comparing a SPOS of each of the PPG signal segments used to calculate a composite signal against the SPOS of the calculated composite signal,
removing outlier PPG signal segments,
re-calculating the composite signal with the outlier PPG signal segments removed, and
repeating the iteration until there are no more outlier PPG signal segments, and measure a person's venous oxygen saturation by:
(a) calculating arterial oxygen saturation by comparing composite signals measured at different wavelengths of light,
(b) sub-sampling composite signals at two consecutive signal maxima measured at different wavelengths of light, and
(c) comparing the sub-sampled composite signals measured at different wavelengths of light to the calculated arterial oxygen saturation to determine venous oxygen saturation.

* * * * *